(12) United States Patent
Mensa-Wilmot

(10) Patent No.: US 8,338,433 B2
(45) Date of Patent: Dec. 25, 2012

(54) TYROSINE KINASE INHIBITORS AS ANTI-KINETOPLASTID AGENTS

(75) Inventor: Kojo Mensa-Wilmot, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 557 days.

(21) Appl. No.: 12/446,286

(22) PCT Filed: Nov. 21, 2007

(86) PCT No.: PCT/US2007/024319
§ 371 (c)(1),
(2), (4) Date: Jul. 1, 2009

(87) PCT Pub. No.: WO2008/066755
PCT Pub. Date: Jun. 5, 2008

(65) Prior Publication Data
US 2010/0311742 A1    Dec. 9, 2010

Related U.S. Application Data

(60) Provisional application No. 60/860,717, filed on Nov. 22, 2006.

(51) Int. Cl.
*A01N 43/54* (2006.01)
*C07D 239/42* (2006.01)
*C07D 401/04* (2006.01)
*A61K 31/505* (2006.01)

(52) U.S. Cl. .................................. 514/256; 514/275

(58) Field of Classification Search .............. 514/256
See application file for complete search history.

(56) References Cited

U.S. PATENT DOCUMENTS

| | | |
|---|---|---|
| 3,470,182 A | 9/1969 | Hardtmann et al. |
| 3,551,427 A | 12/1970 | Ott et al. |
| 3,772,295 A | 11/1973 | Robba et al. |
| 3,800,039 A | 3/1974 | Marquis et al. |
| 4,343,940 A | 8/1982 | Kreighbaum et al. |
| 4,464,375 A | 8/1984 | Kobayashi et al. |
| 5,521,184 A | 5/1996 | Zimmermann |
| 5,618,829 A | 4/1997 | Takayanagi et al. |
| 5,639,757 A | 6/1997 | Dow et al. |
| 5,656,643 A | 8/1997 | Spada et al. |
| 5,710,158 A | 1/1998 | Myers et al. |
| 5,714,493 A | 2/1998 | Myers et al. |
| 5,721,237 A | 2/1998 | Myers et al. |
| 5,728,868 A | 3/1998 | Springer et al. |
| 5,792,783 A | 8/1998 | Tang et al. |
| 5,804,396 A | 9/1998 | Plowman |
| 5,834,504 A | 11/1998 | Tang et al. |
| 5,883,113 A | 3/1999 | Tang et al. |
| 5,883,116 A | 3/1999 | Tang et al. |
| 5,886,020 A | 3/1999 | Tang et al. |
| 6,100,254 A | 8/2000 | Budde et al. |
| 6,127,374 A | 10/2000 | Bridges |
| 6,245,759 B1 | 6/2001 | Bilodeau et al. |
| 6,306,874 B1 | 10/2001 | Fraley et al. |
| 6,313,138 B1 | 11/2001 | Fraley et al. |
| 6,316,444 B1 | 11/2001 | Hunt et al. |
| 6,329,380 B1 | 12/2001 | Goulet et al. |
| 6,344,459 B1 | 2/2002 | Bridges et al. |
| 6,420,382 B2 | 7/2002 | Fraley et al. |
| 6,479,512 B1 | 11/2002 | Fraley et al. |
| 6,498,165 B1 | 12/2002 | Armstrong et al. |
| 6,544,988 B1 | 4/2003 | Bilodeau et al. |
| 6,562,818 B1 | 5/2003 | Bridges |
| 6,586,423 B2 | 7/2003 | Bilodeau et al. |
| 6,586,424 B2 | 7/2003 | Bilodeau et al. |
| 6,740,665 B1 | 5/2004 | Murali et al. |
| 6,794,393 B1 | 9/2004 | Fraley et al. |
| 6,875,767 B2 | 4/2005 | Bilodeau et al. |
| 6,927,293 B2 | 8/2005 | Kim et al. |
| 6,958,340 B2 | 10/2005 | Bilodeau et al. |
| 6,984,389 B2 | 1/2006 | Li |
| 7,189,820 B2 | 3/2007 | Ruben |
| 2001/0044451 A1 | 11/2001 | Fraley et al. |
| 2001/0047007 A1 | 11/2001 | Fraley et al. |
| 2002/0147203 A1 | 10/2002 | Bilodeau et al. |
| 2003/0059862 A1 | 3/2003 | Ruben |
| 2003/0064996 A1 | 4/2003 | Bilodeau et al. |
| 2003/0092145 A1 | 5/2003 | Jira et al. |
| 2003/0100567 A1 | 5/2003 | Bilodeau et al. |
| 2003/0203846 A1 | 10/2003 | Srivastava et al. |
| 2004/0192725 A1 | 9/2004 | Kim et al. |
| 2004/0220201 A1 | 11/2004 | Bilodeau et al. |
| 2005/0096344 A1 | 5/2005 | Fraley et al. |

(Continued)

FOREIGN PATENT DOCUMENTS

EP    0 520 722 A1    12/1992

(Continued)

OTHER PUBLICATIONS

Wheeler-Alm et al. ( Evidence of Tyrosine Kinase Activity in the Protozoan Parasite *Trypanosoma brucei*. Journal of Eukaryotic Microbiology vol. 39, Issue 3, pp. 413-416, May 1992).*

Croft et al. (The activities of four anticancer alkyllysophospholipids against *Leishmania donovani*, *Trypanosoma cruzi* and *Trypanosoma brucei*. Journal of Antimicrobial Chemotherapy (1996) 38, 1041-1047).*

Wheeler-Aim et al. ( Evidence of Tyrosine Kinase Activity in the Protozoan Parasite *Trypanosoma brucei*. Journal of Eukaryotic Microbiology vol. 39, Issue 3, pp. 413-416, May 1992).*

Ghansah et al. (Epidermal growth factor binds to a receptor on *Trypanosoma cruzi* amastigotes inducing signal transduction events and cell proliferation J Eukaryot Microbiol. Sep.-Oct. 2002;49(5):383-90).*

(Continued)

*Primary Examiner* — Sreeni Padmanabhan
*Assistant Examiner* — Layla Soroush
(74) *Attorney, Agent, or Firm* — Mueting Raasch & Gebhardt, P.A.

(57) ABSTRACT

The present invention provides methods of killing, inhibiting the growth, and/or inhibiting the reproduction of kine-toplastid or apicomplexan protozoan with tyrosine kinase inhibitors.

11 Claims, 6 Drawing Sheets

U.S. PATENT DOCUMENTS

| | | | |
|---|---|---|---|
| 2007/0160603 | A1 | 7/2007 | Ruben |
| 2008/0274107 | A1 | 11/2008 | Fraley et al. |
| 2009/0202625 | A1 | 8/2009 | Mensa-Wilmot et al. |

FOREIGN PATENT DOCUMENTS

| | | | |
|---|---|---|---|
| EP | 0 602 851 A1 | 6/1994 | |
| EP | 0 602 851 B1 | 1/1996 | |
| EP | 0 520 722 B1 | 12/1996 | |
| EP | 0 584 222 B1 | 10/1997 | |
| EP | 1 262 556 A2 | 12/2002 | |
| WO | WO 92/20642 A1 | 11/1992 | |
| WO | WO 95/15758 A1 | 6/1995 | |
| WO | WO 96/40116 A1 | 12/1996 | |
| WO | WO 99/03854 A1 | 1/1999 | |
| WO | WO 00/38519 A1 | 7/2000 | |
| WO | WO 2008/006085 A2 | 1/2008 | |
| WO | WO 2008/021092 A2 | 2/2008 | |
| WO | WO 2008/021092 A3 | 9/2008 | |
| WO | WO 2008/006085 A3 | 4/2009 | |

OTHER PUBLICATIONS de la Canal, et al. "Synthesis of Dolichol Derivatives in Trypanosmatids Characterization of Enzymatic Patterns," 1987. Journal of Biological Chemistry. pp. 11128-11133.

El Moudni et al., "Purification and Characterization of N-Acetylglucosaminidase from *Trypanosoma cruzi*," 1996. Experimental Parasitology, 83, 167-173. Article No. 0063.

Vidugiriene et al. "The GPI Anchor of Cell-Surface Proteins Is Synthesized on the Cytoplasmic Face of the Endoplasmic Reticulum," 1994. Journal of Cell Biology, 127(2):333-341.

Akita and Sliwkowski, "Preclinical studies with Erlotinib (Tarceva)," Jun. 2003 *Semin. Oncol.* 30(3 Supp. 7):15-24.

Bennett et al., "Cytochrome oxidase inhibition: a novel animal model of Alzheimer's disease," Apr.-Jun. 1992 *J. Geriatr. Psychiatry Neurol.* 5(2):93-101.

Berridge et al., "Tetrazolium dyes as tools in cell biology: new insights into their cellular reduction," 2005 *Biotechnol. Ann. Rev.* 11:127-152.

Blagosklonny et al., "Geldanamycin selectively destabilizes and conformationally alters mutated p53," Sep. 7, 1995 *Oncogene* 11(5):933.

Bolen, "Nonreceptor tyrosine protein kinases," Aug. 1993 *Oncogene* 8(8):2025-2031.

Bulgaru et al., "Erlotinib (Tarceva®): a promising drug targeting epidermal growth factor receptor tyrosine kinase," Jun. 2003 *Exp. Rev. Anticancer Ther.* 3(3):269-279.

Caplan et al., "YDJ1p facilitates polypeptide translocation across different intracellular membranes by a conserved mechanism," Dec. 24, 1992 *Cell* 71(7):1143-1155.

Chan et al., "Selective inhibition of the growth of ras-transformed human bronchial epithelial cells by emodin, a protein-tyrosine kinase inhibitor," Jun. 30, 1993 *Biochem. Biophys. Res. Comm.* 193(3):1152-1158.

Chan et al., "Three new flavonoids and antiallergic, anti-inflammatory constituents from the heartwood of *Dalbergia odorifera*," Mar. 1998 *Planta. Med.* 64:153-158.

Chirico et al., "70K heat shock related proteins stimulate protein translocation into microsomes," Apr. 28, 1988 *Nature* 332(6167):805-810.

Corbett et al., "Response of transplantable tumors of mice to anthracenedione derivatives alone and in combination with clinically useful agents," May 1982 *Cancer Treatment Reports* 66(5):1187-1200.

Cross, "Identification, purification and properties of clone-specific glycoprotein antigens constituting the surface coat of *Trypanosoma brucei*," Dec. 1975 *Parasitol.* 71(3):393-417.

Crowley et al., "Secretory proteins move through the endoplasmic reticulum membrane via an aqueous, gated pore," Aug. 12, 1994 *Cell* 78(3):461-471.

Dewji, "Early phase I data on an irreversible pan-erb inhibitor: CI-1033. What did we learn?" Nov. 2004 *J. Chemother.* 16(Supp. 4):44-48.

Fradelizi et al., "Quantitative measurement of proteins by western blotting with Cy5™—coupled secondary antibodies," Mar. 1999 *Biotechniques* 26(3):484, 486, 488, 490, 492-494.

Gallagher, "One-dimensional SDS gel electrophoresis of proteins," Chapter 6: Unit 6.1 in *Current Protocols in Cell Biology*; John Wiley & Sons: Hoboken, NJ. Dec. 2007. Supplement 37, pp. 6.1.1-6.1.38.

Gorlich et al., "A mammalian homolog of SEC61 p and SECYp is associated with ribosomes and nascent polypeptides during translocation," Oct. 30, 1992 *Cell* 71(3):489-503.

Hamid, "Emerging trea ments in oncology: focus on tyrosine kinase (erbB) receptor inhibitors," Jan.-Feb. 2004 *J. Am. Pharm Assoc.* 44(1):52-58.

Hammarton et al., "The cell cycle of parasitic protozoa: potential for chemotherapeutic exploitation," 2003 *Prog. Cell Cycle Res.* 5:91-101.

Hansen et al., "In vitro protein translocation across the yeast endoplasmic reticulum: ATP-dependent posttranslational translocation of the prepro-α-factor," May 9, 1986 *Cell* 45(3):397-406.

Hellwig et al., "Altersetin, a new antibiotic from cultures of endophytic *Alternaria* spp. Taxonomy, fermentation, isolation, structure elucidation and biological activities," Oct. 2002 *J. Antibiot (Tokyo)* 55(10):881-892.

Hirumi and Hirumi, "In vitro cultivation of *Trypanosoma conolense* bloodstream forms in the absence of feeder cell layers," Apr. 1991 *Parasitol.* 102(Pt 2):225-236.

Meydan et al., "Inhibition of acute lymphoblastic leukaemia by a Jak-2 inhibitor," Feb. 15, 1996 *Nature* 379(6566):645-648.

O'Dell et al., "Long-term potentiation in the hippocampus is blocked by tyrosine kinase inhibitors," Oct. 10, 1991 *Nature* 353(6344):558-560.

Rusch and Kendall, "Protein transport via amino-terminal targeting sequences: common themes in diverse systems," Oct.-Dec. 1995 *Mol. Membr. Biol.* 12(4):295-307.

Ryan et al., "Overall signal sequence hydrophobicity determines the in vivo translocation efficiency of a herpesvirus glycoprotein," Feb. 1993 *Virus Genes* 7(1):5-21.

Schwartz et al., "Induction of the differentiated phenotype in human colon cancer cells is associated with the attenuation of subcellular tyrosine phosphorylation," 1995 *Oncol. Res.* 7(6):277-287.

Shimizu and Hendershot, "Organization of the functions and components of the endoplasmic reticulum," Chapter 4 in *Molecular Aspects of the Stress Response: Chaperones, Membranes and Networks*. Cseimely and Vigh (Eds.) Landes Bioscience and Springer Science + Business Media: Boston, MA; 2007. Title page and pp. 37-46.

Simon and Blobel, "A protein-conducting channel in the endoplasmic reticulum," May 3, 1991 *Cell* 65(3):371-380.

Sugie et al., "CJ-21,058, a new SecA inhibitor isolated from a fungus," Jan. 2002 *J. Antibiot (Tokyo)* 55(1):25-29.

Umezawa et al., "Inhibition of epidermal growth factor-induced DNA synthesis by tyrosine kinase inhibitors," Jan. 29, 1990 *FEBS Lett.* 260(2):198-200.

Vesonder et al., "Equisetin, an antibiotic from *Fusarium equiseti* NRRL 5537, identified as a derivative of N-methyl-2,4-pyrollidone," Jul. 1979 *J. Antibiot. (Tokyo)* 32(7):759-761.

Vickerman, "Developmental cycles and biology of pathogenic trypanosomes," Apr. 1985 *Br. Med. Bull.* 41(2):105-114.

Walter and Blobel, "Preparation of microsomal membranes for cotranslational protein translocation," 1983 *Methods Enzymol.* 96:84-93.

Wheeler-Alm and Shapiro, "Glycosome-associate tyrosine-phosphorylated protein in *Trypanosoma brucei*," Dec. 1993 *Trop. Med. Parasitol.* 44(4):281-284.

Wiedmann et al., "*Xenopus* oocytes can secrete bacterial β-lactamase," 1984 *Nature* 309:637-639.

Wilks, "Protein tyrosine kinase growth factor receptors and their ligands in development, differentiation, and cancer," 1993 *Adv. Cancer Res.* 60:43-73.

Woods-Ignatoski, "Immunoprecipitation and western blotting of phosphotyrosine-containing proteins," 2001 *Methods Mol. Bio.* 124:39-48.

Yamaki et al., "Inhibition of *c-myc* gene expression in murine lymphoblastoma cells by geldanamycin and herbimycin, antibiotics of benzoquinoid ansamycin group," Apr. 1989 *J. Antibiot. (Tokyo)* 42(4):604-610.

Abrahmsen et al., "Analysis of signals for secretion in the staphylococcal protein a gene," Dec. 30, 1985 *EMBO J.* 4(13B):3901-3906.

Abrams et al., "SU11248 inhibits KIT and platelet-derived growth factor receptor β in preclinical models of human small cell lunch cancer," May 2003 *Mol Cancer Ther.* 2(5):471-478.

Akiyama et al., "Genistein, a specific inhibitor of tyrosine-specific protein kinases," Apr. 25, 1987 *J. Biol. Chem.* 262(12):5592.

Albuschat et al., "4-anilinoquinazolines with Lavendustin A subunit as inhibitors of epidermal growth factor receptor tyrosine kinase: syntheses, chemical and pharmacological properties," Dec. 2004 *Eur. J. Med. Chem.* 39(12):1001-1011.

Al-Qahtani and Mensa-Wilmot, "A 5' untranslated region which directs accurate and robust translation by prokaryotic and mammalian ribosomes," Mar. 15, 1996 *Nucleic Acid Res.* 24(6):1173-1174.

Al-Qahtani et al., "Species-specificity in endoplasmic reticulum signal peptide utilization revealed by proteins from *Trypanosoma brucei* and *Leishmania*," Apr. 15, 1998 *Biochem J.* 331(Pt 2):521-529.

Alberts et al., *Molecular Biology of the Cell 3rd Edition*. Garland Publishing: New York, NY. 1994. Cover page, publishers page and pp. 577-594.

Anafi et al., "Selective interactions of transforming and normal *abl* proteins with ATP, tyrosine-copolymer substrates, and tyrphostins," Mar. 5, 1992 *J. Biol. Chem.* 26(7)7:4518-4523.

Aparna et al., "Virtual screening of 4-anilinoquinazoline analogues as EGFR kinase inhibitor: importance of hydrogen bonds in the evaluation of poses and scoring functions," May-Jun. 2005 *J. Chem. Inf. Model* 45(3):725-738.

Assefa et al., "3D-QSAR and docking studies on 4-anilinoquinazoline and 4-anilinoquinoline epidefinal growth factor receptor (EGR) tyrosine kinase inhibitors," Aug. 2003 *J. Comput. Aided Mol. Des.* 17(8):475-493.

Attoub et al., "The c-kit tyrosine kinase inhibitor STI571 for colorectal cancer therapy," Sep. 1, 2002 *Cancer Res.* 62(17):4879-4883.

Axitinib product datasheet [online]. Pfizer Oncology; New York, NY. Published in 2008 [retrieved on May 18, 2009]. Retrieved from the Internet: <http://media.pfizer.com/files/news/asco/axitinib_fact_sheet_2008.pdf; 1 pg.

"Axitinib shows promise in treatment of advanced thyroid cancer," Jun. 7, 2007 *News-Medical.Net*. Available online [retrieved on Nov. 16, 2007]. Retrieved from the Internet: <http://wvvw.news-medical.net/print_article.asp?id=26022>; 2 pgs.

Bangs et al., "Posttranslational modification and intracellular transport of a trypanosome variant surface glycoprotein," Jul. 1986 *J. Cell Biol.* 103(1):255-263.

Bangs et al., "A soluble secretory reporter system in *Trypanosoma brucei*. Studies on endoplasmic reticulum targeting," Aug. 2, 1996 *J. Biol. Chem.* 271(31):18387-18393.

Barrett et al., "Recent advances in identifying and validating drug targets in trypanosomes and *Leishmanias*," Feb. 1999 *Trends Microbiol.* 7(2):82-88.

Barrett and Barrett, "Anti-sleeping sickness drugs and cancer chemotherapy," Jan. 2000 *Parasitol. Today* 16(1):7-9.

Barrett et al., "Human African trypanosomiases: pharmacological re-engagement with a neglected disease," Dec. 2007 *Br. J. Pharmacol.* 152(8):1155-1171. Available online on Jul. 9, 2007.

Barrett et al., "The discovery of the benzhydroxamate MEK inhibitors CI-1040 and PD 0325901," Dec. 15, 2008 *Bioorg. Med. Chem. Lett.* 18(24):6501-6504. Available online on Oct. 15, 2008.

Batra et al., "Epidermal growth factor ligand-independent, unregulated, cell-transforming potential of a naturally occurring human mutant *EGFRvIII* gene," Oct. 1995 *Cell Growth Diff.* 6(10):1251-1259.

Becker et al., "Functional interaction of cytosolic hsp70 and a DnaJ-related protein, Ydj1p, in protein translocation in vivo," Aug. 1996 *Mol. Cell Biol.* 16(8):4378-4386.

Besemer et al., "Selective inhibition of cotranslational translocation of vascular cell adhesion molecule 1," Jul. 14, 2005 *Nature* 436(7048):290-293.

Bilder et al., "Tyrphostins inhibit PDGF-induced DNA synthesis and associated early events in smooth muscle cells," Apr. 1991 *Am. J. Physiol.—Cell Physiol.* 260:C721-C730.

Bird et al., "Translocation in yeast and mammalian cells: not all signal sequences are functionally equivalent," Dec. 1987 *J. Cell Biol.* 105(6 Pt2):2905-2914.

Bleasdale et al., "Small molecule peptidominretics containing a novel phosphotyrosine biosostere inhibit protein tyrosine phosphatase 1B and augment insulin action," May 15, 2001 *Biochem.* 40(19):5642-5654.

Bowler et al., "How azide inhibits ATP hydrolysis by the F-ATPases," Jun. 6, 2006 *PNAS* 103(23):8646-8649. Available online on May 25, 2006.

Bridges et al., "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor," Jan. 5, 1996 *J. Med Chem.* 39:267.

Brodsky et al., "Reconstitution of protein translocation from solubilized yeast membranes reveals topologically distinct roles for BiP and cytosolic Hsc70," Jan. 1993 *J. Cell Biol.* 120(1):95-102.

Brodsky et al., "BiP and Sec63p are required for both co- and post-translational protein translocation into the yeast endoplasmic reticulum," Oct. 10, 1995 *PNAS* 92(21):9643-9646.

Brodsky and Chiosis, "Hsp70 molecular chaperones: emerging roles in human disease and identification of small molecule modulators," 2006 *Curr. Top. Med. Chem.* 6(11):1215-1225.

Broniscer et al., "Plasma and cerebrospinal fluid pharmacokinetics of erlotinib and its active metabolite OSI-420," Mar. 1, 2007 *Clin Cancer Res.* 13(5):1511-1515.

Bruch and Gierasch, "Comparison of helix stability in wild-type and mutant LamB signal sequences," Mar. 5, 1990 *J. Biol. Chem.* 265(7):3851-3858.

Bryckaert et al., "Inhibition of platelet-derived growth factor-induced mitogenesis and tyrosine kinase activity in cultured bone marrow fibroblasts by tyrphostins," Apr. 1992 *Exp. Cell Res.* 199(2):255-261.

Burke et al., "A short stereoselective total synthesis of the fusarium toxin equisetin," Nov. 16, 2000 *Org. Lett.* 2(23):3611-3613.

Button et al., "Recombinant *Leishmania* surface glycoprotein GP63 is secreted in the baculovirus expression system as a latent metalloproteinase," Nov. 30, 1993 *Gene* 134(1):75-81.

Cabebe and Wakelee, "Sunitinib: a newly approved small-molecule inhibitor of angiogenesis," Jun. 2006 *Drugs Today* 42(6):387-398.

Carter et al., "Inhibition of drug-resistance mutants of ABL, KIT, and EGF receptor kinases," Aug. 2, 2005 *PNAS* 102(31):11011-11016. Available online on Jul. 26, 2005.

Chen et al., "Synthesis and structure-activity studies of a series of [(hydroxybenzyl)amino]salicylates as inhibitors of EGF receptor-associated tyrosine kinase activity," Dec. 10, 1993 *J. Med. Chem.* 36(25):4094-4098.

Chen et al., "Competition between functional signal eptides demonstrates variation in affinity for the secretion pathway," Dec. 1996 *J. Bacteriol.* 178(23):6658-6664.

Chini et al., "Evidence that the cADPR signaling pathway controls calcium-mediated microneme secretion in *Toxoplasma gondii*," 2005 *Biochem J.* 389:269-277.

Chopard et al., "Quantitative analysis of relative protein contents by Western blotting: comparison of three members of the dystrophin-glycoprotein complex in slow and fast rat skeletal muscle," Feb. 2000 *Electrophoresis* 21(3):517-522.

Chou and Kendall, "Polymeric sequences reveal a functional inter-relationship between hydrophobicity and length of signal peptides," Feb. 15, 1990 *J Biol. Chem.* 265(5):2873-2880.

Chu et al., "Receptor dimerization is not a factor in the signalling activity of transforming variant epidermal growth factor receptor (EGFRvIII)," Jun. 15, 1997 *Biochem. J.* 324(Pt 3):855-861.

CI-1033 (Canertinib®) product website [online]. Selleck Chemicals Co., Ltd.: London, Ontario, Canada. Copyright 2009 [retrieved on May 8, 2009]. Retrieved from the Internet: <http://www.selleckchem.com/ProductDetail.asp?ProdId=S1019>; 2 pgs.

Clemons et al., "Structural insight into the protein translocation channel," Aug. 2004 Curr. Opin. Struct. Biol. 14(4):390-396. Available online on Jul. 21, 2004.

Connolly et al., "Access of proteinase K to partially translocated nascent polypeptides in intact and detergent-solubilized membranes," Feb. 1989 J. Cell Biol. 108(2):299-307.

Cowman and Crabb, "Functional genomics: identifying drug targets for parasitic diseases," Nov. 2003 Trends Parasitol. 19(11):538-543.

Cushman et al., "Synthesis and protein-tyrosine kinase inhibitory activities of flavonoid analogues," Feb. 1991 J. Med. Chem. 34(2):798-806.

Cyr and Douglas, "Differential regulation of Hsp70 subfamilies by the eukaryotic DnaJ homologue YDJ1," Apr. 1, 1994 J. Biol. Chem. 269(13):9798-9804.

Dai et al., "Discovery of N-(4-(3-amino-1H-indazol-4-yl)phenyl)-N'-(2-fluoro-5-methylphenyl)urea (ABT-869), a 3-aminoindazole-based orally active multitargeted receptor tyrosine kinase inhibitor," Apr. 5, 2007 J. Med. Chem. 50(7):1584-1597. Available online on Mar. 8, 2007.

Dardonville et al., "DNA binding affinity of bisguanidine and bis(2-aminoimidazoline) derivativeswith in vivo antitrypanosomal activity," Jun. 15, 2006 J. Med. Chem. 49(12):3748-3752. Available online on May 23, 2006.

Das et al., "2-aminothiazole as a novel kinase inhibitor template. Structure-activity relationship studies toward the discovery of N-(2-chloro-6-methylphenyl)-2-[[6-[4-(2-hydroxyethyl)-1-piperazinyl)]-2-methyl-4-pyrimidinyl]amino)]-1,3-thiazole-5-carboxamide (dasatinib, BMS-354825) as a potent pan-Src kinase inhibitor," Nov. 16, 2006 J. Med. Chem. 49(23):6819-6823. Available online on Oct. 24, 2006.

De Clercq, "Current lead natural products for the chemotherapy of human immunodeficiency virus (HIV) infection," Sep. 2000 Med. Res. Rev. 20(5):323-349.

De Koning, "Transporters in African trypanosomes: role in drug action and resistance," May 1, 2001 Int. J. Parasitol. 31(5-6):512-521.

Del Rayo Camacho et al., "In vitro activity of Triclisia patens and some bisbenzylisoquinoline alkaloids against Leishmania donovani and Trypanosoma brucei brucei," Aug. 2002 Phytother. Res. 16(5):432-436.

Denny, "The 4-anilinoquinazoline class of inhibitors of the erbB family of receptor tyrosine kinases," Jan.-Feb. 2001 Farmaco 56(1-2):51-56.

Detimary et al., "Two sites of glucose control of insulin release with distinct dependence on the energy state in pancreatic B-cells," Feb. 1, 1994 Biochem J. 297(Pt 3):455-461.

Docampo and Moreno, "Current chemotherapy of human African trypanosomiases," Jun. 2003 Parasitol. Res. 90(Supp. 1):S10-13. Available online on Nov. 23, 2002.

Doud et al., "Titration of protein transport activity by incremental changes in signal peptide hydorphobicity," Feb. 9, 1993 Biochem. 32(5):1251-1256.

Dovey et al., "Biogenesis of glycosomes on Trypanosoma brucei: an in vitro model of 3-phosphoglycerate kinase import," Apr. 1988 PNAS 85(8):2598-2602.

Driessen et al., "The structural basis of protein targeting and translocation in bacteria," Jun. 2001 Nat. Struct. Biol. 8(6):492-498.

Duffy, Joshua, "Protein translocation into the endoplasmic reticulum of Trypanosoma brucei," Doctoral Thesis; University of Georgia. Cover Date Dec. 2008.

El-Sayed and Donelson, "African tyrpanosomes have differentially expressed genes encoding homologues of the Leishmania GP63 surface protease," Oct. 17, 1997 J. Biol. Chem. 272(42):26742-26748.

Ellis et al., "Preclinical analysis of the analinoquinazoline AG1478, a specific small molecule inhibitor of EGF receptor tyrosine kinase," May 14, 2006 Biochem Pharmacol. 71(10):1422-1434. Available online on Mar. 7, 2006.

Fairlamb, "Chemotherapy of human African trypanosomiases: current and future prospects," Nov. 2003 Trends Parasitol. 19(11):488-494.

Faltynek et al., "Damnacanthal is a highly potent, selective inhibitor of p561ck tyrosine kinase activity," Sep. 26, 1995 Biochemistry 34(38):12404-12410.

Fekkes et al., "Preprotein transfer to the Escherichia coli translocase requires the co-operative binding of SecB and the signal sequence to SecA," Sep. 1998 Mol. Microbiol. 29(5):1179-1190.

Fewell et al., "Identification of an inhibitor of hsc70-mediated protein translocation and ATP hydrolysis," Jan. 12, 2001 J. Biol. Chem. 276(2):910-914. Available online on Oct. 17, 2000.

Fewell et al., "Small molecule modulators of endogenous and co-chaperone-stimulated Hsp70 ATPase activity," Dec. 3, 2004 J. Biol. Chem. 279(49):51131-51140. Available online on Sep. 23, 2004.

Fong et al., "SU5416 is a potent and selective inhibitor of the vascular endothelial growth factor receptor (Flk-1/KDR) that inhibits tyrosine kinase catalysis, tumor vascularization, and growth of multiple tumor types," Jan. 1, 1999 Cancer Res. 59(1):99-106.

Fry et al., "A specific inhibitor of the epidermal growth factor receptor tyrosine kinase," Aug. 19, 1994 Science 265(5175):1093-1095.

Fukazawa et al., "Specific inhibition of cytoplasmic protein tyrosine kinases by herbimycin A in vitro," Oct. 9, 1991 Biochem. Pharmacol. 42(9):1661-1671.

Garcia and Walter, "Full-length prepro-alpha-factor can be translocated across the mammalian microsomal membrane only if translation has not terminated," Apr. 1988 J. Cell Biol. 106:1043-1048.

Garrison et al., "A substrate-specific inhibitor of protein translocation into the endoplasmic reticulum," Jul. 14, 2005 Nature 436:285-289.

Gazit et al., "Tyrphostins I: synthesis and biological activity of protein tyrosine kinase inhibitors," Oct. 1989 J. Med. Chem. 32(10):2344-2352.

Gazit et al., "Tyrphostins. 2. Heterocyclic and alpha-substituted benzylidenemalononitrile tyrphostins as potent inhibitors of EGF receptor and ErbB2/ney tyrosine kinases," Jun. 1991 J. Med. Chem. 34(6):1896-1907.

Gelb and Hol, "Drugs to combat tropical protozoan parasites," Jul. 19, 2002 Science 297(5580):343-344.

Gelb et al., "Protein farnesyl and N-myristoyl transferases: piggyback medicinal chemistry targets for the development of antitrypanosomatid and antimalarial therapeutics," Feb. 2003 Mol. Biochem. Parasitol. 126(2):155-163.

George et al., "Antikinetoplastid antimitotic activity and metabolic stability of dinitroaninline sulfonamides and benzamides," Aug. 15, 2006 Bioorg. Med. Chem. 14(16):5699-5710. Available online on May 3, 2006.

Ghosh et al., "Structure-based design of potent inhibitors or EGF-receptor tyrosine kinase as anti-cancer agents," Oct. 1999 Anticancer Drug Des. 14(5):403-410.

Gilmore et al., "Protein Translocation Across the Endoplasmic Reticulum. I. Detection in the Microsomal Membrane of a Receptor for the Signal Recognition Particle," Nov. 1982 J. Cell. Biol. 95(2 Pt 1):463-469.

Gleevec® (imatinib mesylate) product website " How Gleevec® works," [online]. Novartis Oncology; East Hanover, NJ. Copyright 2009 [retrieved on April 28, 2009]. Retrieved from the Internet: <http://www.gleevec.com/info/ag/index.jsp?print=yes>; 1 pg.

Goldshmidt et al., "Role of protein in translocation pathways across the endoplasmic reticulum in Trypanosoma brucei," Nov. 14, 2008 J. Biol. Chem. 283(46):32085-32098. Available online on Sep. 2, 2008.

Green et al, "Inhibitors of tumor progression loci-2 (Tpl2) kinase and tumor necrosis factor alpha (TNF-alpha) production: selectivity and in vivo antiinflammtory activity of novel 8-substituted-4-anilino-6-aminoquinoline-3-carbonitriles," Sep. 20, 2007 J. Med. Chem. 50(19):4728-4745. Available online on Aug. 23, 2007.

Gridelli et al., "Sorafenib and sunitinib in the treatment of advanced non-small cell lung cancer," Feb. 2007 Oncologist 12(2):191-200.

Gull, "The cell biology of parasitism in Trypanosoma brucei: insights and drug targets form genomic approaches?" 2002 Curr. Pharm. Des. 8(4):241-256.

Haeuptle et al., A tripartite structure of the signals that determine protein insertion into the endoplasmic reticulum membrane, Apr. 1989 J. Cell. Biol. 108(4):1227-1236.

Hanke et al., "Discovery of a novel, potent, and Src family-selective tyrosine kinase inhibitor. Study of Lck- and FynT-dependent T cell activation," Jan. 12, 1996 J. Biol. Chem. 271(2):695-701.

Harant et al., "The translocation inhibitor CAM741 interferes with vascular cell adhesion molecule 1 signal peptide insertion at the translocon," Oct. 13, 2006 *J. Biol. Chem.* 281(41):30492-30502. Available online on Aug. 16, 2006.

Harant et al., "Inhibition of vascular endothelial growth factor cotranlsational translocation by the cyclopeptolide CAM741," Jun. 2007 *Mol. Pharmacol.* 71(6):1657-1665. Available online on Mar. 16, 2007.

Hegde and Bernstein, "The surprising complexity of signal sequences," Oct. 2006 *Trends Biochem. Sci.* 31(10):563-571. Available online on Aug. 21, 2006.

Hennequin et al., "Novel 4-anilinoquinazolines with C-6 carbon-linked side chains: synthesis and structure-activity relationship of a series of potent, orally active, EGF receptor tyrosine kinase, May 15, 2006 *Bioorg. Med. Chem. Lett.* 16(10):2672-2676. Available online on Mar. 3, 2006.

Heymach et al., "Epidermal growth factor receptor inhibitors in development for the treatment of non-small cell lung cancer," Jul. 15, 2006 *Clin.Cancer Res.* 12(14 Pt 2):4441s-4445s.

Himpens et al., "Modulation of nucleocytosolic [Ca2+] gradient in smooth muscle by protein phosphorylation," Aug. 1994 *FASEB J.* 8(11):879-883.

Hirumi and Hirumi, "Axenic culture of African trypanosome bloodstream forms," Feb. 1994 *Parasitol. Today* 10(2):80-84.

Holkeri et al., "Dissection of the translocation and chaperoning functions of yeast BiP/Kar2p in vivo," Mar. 1998 *J. Cell Sci.* 111(Pt 6):749-757. Available online on Feb. 23, 1998.

Hubbard and Till, "Protein tyrosine kinase structure and function," 2000 *Ann. Rev. Biochem.* 69:373-398.

Innis et al., "DNA sequencing with *Thermus aquaticus* DNA polymerase and direct sequencing of polymerase chain reaction-amplified DNA," Dec. 1988 *PNAS* 85(24):9436-9440.

International Preliminary Report on Patentability issued on Feb. 10, 2009, in PCT/US2007/017555; 6 pgs.

International Preliminary Report on Patentability issued on May 26, 2009, in PCT/US2007/024319; 6 pgs.

International Search Report and Written Opinion of the International Searching Authority issued on Jun. 17, 2008, in PCT/US2007/017555; 11 pgs.

International Search Report and Written Opinion of the International Searching Authority issued on Nov. 10, 2008, in PCT/US2007/024319; 9 pgs.

Izard and Kendall, "Signal peptides: exquisitely designed transport promoters," Sep. 1994 *Mol. Microbiol.* 13(5):765-773.

Johnson and Hunter, "Kinomics: methods for deciphering the kinome," Jan. 2005 *Nat. Methods* 2(1):17-25. Available online on Dec. 21, 2004.

Johnson and van Waes, "The translocon: a dynamic gateway at the ER membrane," 1999 *Ann. Rev. Cell Dev. Biol.* 15:799-842.

Jonassen et al., "Finding flexible patterns in unaligned protein sequences," Aug. 1995 *Protein Sci.* 4(8):1587-1595.

Jungnickel and Rapoport, "A posttargeting signal sequence recognition event in the endoplasmic reticulum membrane," Jul. 28, 1995 *Cell* 82(2):261-270.

Kaiser et al., "Many random sequences functionally replace the secretion signal sequence f yeast invertase," Jan. 16, 1987 *Science* 235(4786):312-317.

Kantarjian et al., "Nilotinib in imatinib-resistant CML and Philadelphia chromosome-positive ALL," Jun. 15, 2006 *New Engl. J. Med.* 354(24):2542-2551.

Kim et al., "An orally administered multitarget tyrosine kinase inhibitor, SU11248, is a novel potent inhibitor of thyroid oncogenic RET/papillary thyroid cancer kinases," Oct. 2006 *J. Clin. Endocrin. Metab.* 91(10):4070-4076. Available online on Jul. 18, 2006.

Knight and Shokat, "Features of selective kinase inhibitors," Jun. 24, 2005 *Chem. Biol.* 12(6):621-637.

Knott and Robinson, "The secA inhibitor, azide, reversibly blocks the translocation of a subset of proteins across the chloroplast thylakoid membrane," Mar. 18, 1994 *J. Biol. Chem.* 269(11):7843-7846.

Konrad et al., "Glucose-induced tyrosine phosphorylation of p125 in beta cells and pancreatic islets. A novel proximal signal in insulin secretion," Sep. 27, 1996 *J. Biol. Chem.* 271(39):24179-24186.

Kovalenko et al., "Selective platelet-derived growth factor receptor kinase blockers reverse *sis*-transformation," Dec. 1, 1994 *Cancer Res.* 54:6106-6114.

Kroll and Waltenberger, "The vascular endothelial growth factor receptor KDR activates multiple signal transduction pathways in porcine aortic endothelial cells," Dec. 19, 1997 *J. Biol. Chem.* 272(51):32521-32527.

Kumar et al., "Small molecule approach to studying protein tyrosine phosphatase," Jan. 2005 *Methods* 35(1):9-21.

Kwon et al., "Potent and specific inhibition of p60$^{v-src}$ protein kinase both in vivo and in vitro by radicicol," Dec. 15, 1992 *Cancer Res.* 52(24):6926-6930.

Laforet et al., "Signal peptide subsegments are not always functionally interchangeable. M13 procoat hydrophobic core fails to transport alkaline phosphatase in *Escherichia coli*," Aug. 25, 1989 *J. Biol. Chem.* 264(24):14478-14485.

Letts and Zimmerman, "Polypeptide synthesis with microsomes from pressure-treated *Tetrahymena*," 1970 *J. Protozool.* 17(4):593-596.

Levitzki, "Tyrphostins—potential antiproliferative agents and novel molecular tools," Sep. 1, 1990 *Biochem. Pharmacol.* 40(5):913-918.

Levitzki and Gilon, "Tyrphostins as molecular tools and potential antiproliferative drugs," May 1991 *Trends Pharmacol. Sci.* 12(5):171-174.

Levitzki, "Tyrphostins: tyrosine kinase blockers as novel antiproliferative agents and dissectors of signal transduction," Nov. 1992 *FASEB J.* 6(14):3275-3282.

Levitzki and Gazit, "Tyrosine kinase inhibition: an approach to drug development," Mar. 24, 1995 *Science* 267(5205):1782-1788.

Levitzki and Mishani, "Tyrphostins and other tyrosine kinase inhibitors," 2006 *Ann. Rev. Biochem.* 75:93-109.

Ling et al., "Metabolism and excretion of erlotinib, a small molecule inhibitor of epidermal growth factor receptor tyrosine kinase, in healthy male volunteers," Mar. 2006 *Drug Metab. Dispos.* 34(3):420-426. Available online on Dec. 28, 2005.

Linggi and Carpenter, "ErbB receptors: new insights on mechanisms and biology," Dec. 2006 *Trends Cell Biol.* 16(12):649-656. Available online on Nov. 7, 2006.

Liu et al., "RNA interference of signal peptide-binding protein SRP54 elicits deleterious effects and protein sorting defects in trypanosomes," Dec. 6, 2002 *J. Biol. Chem.* 277(49)47348-47357. Available online on Sep. 19, 2002.

Liu et al., "Synthesis and biological evaluation of substituted 6-alkynyl-4-anilinoquinazoline derivatives as potent EGFR inhibitors," Nov. 15, 2007 *Bioorg. Med. Chem. Lett.* 17(22):6373-6377. Available online on Aug. 28, 2007.

Lustig et al., "Down-regulation of the trypanosomatid signal recognition particle affects the biogenesis of polytopic membrane proteins but not of signal peptide-containing proteins," Oct. 2007 *Eukaryot. Cell* 6(10):1865-1875. Available online on Aug. 22, 2007.

Lyall et al., "Tyrphostins inhibit epidermal growth factor (EGF)-receptor tyrosine kinase activity in living cells and EGF-stimulated cell proliferation," Aug. 25, 1989 *J. Biol. Chem.* 264(24):14503-14509.

Lyman and Scheckman, "Interaction between BiP and Sec63p is required for the completion of protein translocation into the ER of *Saccharomyces cerevisiae*," Dec. 1, 1995 *J. Cell Biol.* 131(5):1163-1171.

Martoglio and Dobberstein, "Snapshots of membrane-translocating proteins," Apr. 1996 *Trends Cell Biol.* 6(4):142-147.

Martoglio and Dobberstein, "Signal sequences: more than just greasy peptides," Oct. 1998 *Trends Cell Biol.* 8(10):410-415.

Matlack et al., "Protein translocation: tunnel vision," Feb. 6, 1998 *Cell* 92(3):381-390.

Matoba and Ogrydziak, "Another factor besides hydrophobicicty can affect signal peptide interaction with signal recognition particle," Jul. 24, 1998 *J. Biol. Chem.* 273(30):18841-18847.

McClellan et al., "Specific molecular chaperone interactions and an ATP-dependent conformational change are required during post-translational protein translocation into the yeast ER," Dec. 1998 *Mol. Biol. Cell* 9(12):3533-3545.

McClellan and Brodsky, "Mutation of the ATP-binding pocket of *SSA1* indicates that a functional interaction between Ssa1p and Ydj1p is required for post-translational translocation into the yeast endoplasmic reticulum," Oct. 2000 *Genetics* 156(2):501-512.

McConville et al., "Secretory pathway of trypanosomatid parasites," Mar. 2002 *Microbiol. Mol. Biol. Rev.* 66(1):122-154.

McKerrow, "Parasitic infections-molecular diagnosis and rational drug design," Sep. 1996 *Biologicals* 24(3):207-208.

Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," Jan. 2003 *Clin. Cancer Res.* 9(1):327-337.

Mensa-Wilmot, Kojo; University of Georgia faculty webpage [online] University of Georgia Center for Drug Discovery [retrieved on May 4, 2009]. Retrieved from the Internet: <http://www.uga-cdd.org/facultydetail.php?id=43>; 2 pgs.

Mensa-Wilmot, Kojo; University of Georgia faculty webpage [online] University of Georgia Department of Cellular Biology [retrieved on May 4, 2009]. Retrieved from the Internet: <http://www.uga.edu/cellbio/mensa-wilmot.html>; 4 pgs.

Mesa-Wilmot, Kojo "Endoplasmic Reticulum of Trypanosomatids," Grant Abstract, Grant No. 1RO3AI053086-01 [online]. National Institute of Allergy and Infectious Diseases, National Institutes of Health. Project dates Sep. 30, 2002 to Sep. 29, 2004[retrieved on May 4, 2009]. Retrieved from the Internet: <http://crisp.cit.nih.gov/crisp/CRISP_LIB.getdoc?textkey=6556407&p_grant_num=1R03AI053086-01&p_query=&ticket=93590487&p_audit_session_id=463086249&p_keywords=>; 2 pgs.

Mesa-Wilmot, Kojo "Endoplasmic Reticulum of Trypanosomatids," Grant Abstract, Grant No. 5RO3AI053086-02 [online]. National Institute of Allergy and Infectious Diseases, National Institutes of Health. Project dates Sep. 30, 2002 to Sep. 29, 2004[retrieved on May 4, 2009]. Retrieved from the Internet: <http://crisp.cit.nih.gov/crisp/CRISP_LIB.getdoc?textkey=6660348&p_grant_num=5R03AI053086-02&p_query=&ticket=93590487&p_audit_session_id=463086249&p_keywords=>; 2 pgs.

Merkel et al., "Inhibition of EGF-induced vasoconstriction in isolated rabbit aortic rings with the tyrosine kinase inhibitor RG50864," May 14, 1993 *Biochem. Biophys. Res. Comm.* 192(3):1319-1326.

Miller et al., "SecB modulates the nucleotide-bound state of SecA and stimulates ATPase activity," Apr. 23, 2002 *Biochem.* 41(16):5325-5332. Available online on Mar. 29, 2002.

Mitra et al., "Co- and post-translational translocation through the protein-condi=ucting channel: analogous mechanisms at work?" Nov. 2006 *Nat. Struct. Mol. Biol.* 13(11):957-964. Available online on Nov. 3, 2006.

Mohammadi et al., "Structure of the tyrosine kinase domain of fibroblast growth factor receptor in complex with inhibitors," May 9, 1997 *Science* 276(5314):955-960.

Mustafa et al., "Tyrosine kinases are required for interferon-γ-stimulated proliferation of *Trypanosoma brucei* brucei," Mar. 1997 *J. Infect. Dis.* 175(3):669-673.

Naula et al., "Protein kinases as drug targets in trypanosomes and *Leishmania*," Dec. 30, 2005 *Biochim. Biophys. Acta* 1754(1-2):151-159. Available online on Sep. 8, 2005.

Nexavar® (sorafenib) product website [online]. Onyx Pharmaceuticals, Inc.: Emeryville, CA; and Bayer HealthCare Pharmaceuticals, Inc.: Leverkusen, Germany. Copyright 2008 [retrieved on May 13, 2009]. Retrieved from the Internet: <http://www.nexavar-us.com/scripts/pages/en/home/index.php>; 2 pgs.

"Nexavar significantly extends overall survival by 44% in liver cancer patients," Jun. 4, 2007 Onyx Pharmaceuticals, Inc. press release. Available online [retrieved on Nov. 16, 2007]. Retrieved from the Internet: <http://www.onyx-pharm.com/wt/page/pr_1180935729>; 3 pgs.

Ng et al., "Signal sequences specify the targeting route to the endoplasmic reticulum membrane," Jul. 1, 1996 *J. Cell Biol.* 134(2):269-278.

Ngosuwan et al., "Roles of cytosolic Hsp70 and Hsp40 molecular chaperones in post-translational translocation of presecretory proteins into the endoplasmic reticulum," Feb. 28, 2003 *J. Biol. Chem.* 278(9):7034-7042. Available online on Dec. 19, 2002.

Nielsen et al., "Identification of prokaryotic and eukaryotic signal peptides and prediction of their cleavage sites," Jan. 1997 *Protein Eng.* 10(1):1-6.

Novogrodsky et al., "Prevention of lipopolysaccharide-induced lethal toxicity by tyrosine kinase inhibitors," May 27, 1994 *Science* 264(5163):1319-1322.

Nwaka and Ridley, "Virtual drug discovery and development for neglected diseases through public-private partnerships," Nov. 2003 *Nat. Rev. Drug Discov.* 2(11):919-928.

Szende et al., "Tryphostin induces non-apoptotic programmed cell death in colon tumor cells," Nov. 1995 *Cell Biol. Int.* 19(11):903-912.

Tasigna® (nilotinib) product website "Tasigna education" [online]. Novartis Oncology; New Hanover, NJ. Copyright 2007 [retrieved on Apr. 28, 2009]. Retrieved from the Internet: <http://www.us.tasigna.com/info/about-tasigna.jsp?printmode=true>; 3 pgs.

Taylor and Rudenko, "Switching trypanosome coats: what's in the wardrobe?" Nov. 2006 *Trends Genet.* 22(11):614-620. Available online on Aug. 14, 2006.

Teilhet et al., "Effect of short 5' *UTRs* on protein synthesis in two biological kingdoms," Nov. 5, 1998 *Gene* 222(1):91-97.

Thompson and Schultz, "Enzymatic properties of microsomal membranes from the protozoan *Acanthamoeba castellanii*," 1971 *Exp. Cell Res.* 68:106-112.

Tomilo et al., "Can a signal sequence become too hydrophobic?" Dec. 16, 1994 *J. Biol. Chem.* 269(50):32016-32021.

Traxler et al., "Use of a pharmacophore model for the design of EGF-R tyrosine kinase inhibitors: 4-(phenylamino)pyrazolo[3,4-d]pyrimidines," Oct. 24, 1997 *J. Med. Chem.* 40(22):3601-3616. Abstract published on Sep. 15, 1997.

Traxler et al., "AEE788: a dual family epidermal growth factor receptor/ErbB2 and vascular endothelial growth factor receptor tyrosine kinase inhibitor with antitumor and antiangiogenic activity," Jul. 15, 2004 *Cancer Res.* 64(14):4931-4941.

Tsou et al., "Optimization of 6,7-disubstituted-4-(arylamino)quinoline-3-carbonitriles as orally active, irreversible inhibitors of human epidermal growth factor receptor-2 kinase activity," Feb. 24, 2005 *J. Med. Chem.* 48(4):1107-1131. Available online on Jan. 27, 2005.

Turbov et al., "Effects of receptor tyrosine kinase inhibitor A47 on estrogen and growth factor-dependent breast cancer cell proliferation and apoptosis in vitro," Jan. 2002 *J. Surg. Oncol.* 79(1):17-29.

Twaddle et al., "Tyrosine kinase inhibitors as antiproliferative agents against an estrogen-dependent breast cancer cell line in vitro," Feb. 1999 *J. Surg. Oncol.* 70(2):83-90.

Tykerb® (lapatinib) product website "I want more information about Tykerb®" [online]. GlaxoSmithKline Oncology; Brentford, Middlesex UK. Copyright 1997-2009 [retrieved on Apr. 28, 2009]. Retrieved from the Internet: <http://www.tykerb.com/about-tykerb/about-tykerb.html#>; 2 pgs.

"Tyrosine kinase inhibitors," Parker Hughes Institute: St. Paul, MN; copyright 2000. No longer available online [retrieved on Aug. 4, 2006]. Retrieved from the Internet: <www.ih.org/pages/tyrosine_kinase_inhibitors.html>; 2 pgs.

Tzivelka et al., "Natural products with anti-HIV activity from marine organisms," 2003 *Curr. Top. Med. Chem.* 3(13):1512-1535.

Uehara et al., "Irreversible inhibition of v-src tyrosine kinase activity by herbimycin A and its abrogation by sulfhydryl compounds," Sep. 15, 1989 *Biochem. Biophys. Res. Comm.* 163(2):803-809.

Uings et al., "Tyrosine phosphorylation is involved in receptor coupling to phospholipase D but not phospholipase C in the human neutrophil," Feb. 1, 1992 *Biochem. J.* 281(Pt 3):597-600.

Ullers et al., "SecB is a bona fide generalized chaperone in *Escherichia coli*," May 18, 2004 *PNAS* 101(20):7583-7588. Available online on May 5, 2004.

Van de Casteele et al., "Prolonged culture in low glucose induces apoptosis of rat pancreatic β-cells through induction of c-myc," Dec. 26, 2003 *Biochem. Biophys. Res. Comm.* 312(4):937-944.

Van den Berg et al., "X-ray structure of a protein-conducting channel," Jan. 1, 2004 *Nature* 427(6969):36-44. Available online on Dec. 3, 2003.

Van der Ploeg et al., "Heat shock genes: regulatory role for differentiation in parasitic protozoa," Jun. 21, 1985 *Science* 228(4706):1443-1446.

Van der Wolk et al., "The catalytic cycle of the *Escherichia coli* SecA ATPase comprises two distinct preprotein translation events," Dec. 15, 1997 *EMBO J.* 16(24):7297-7304.

Von Heijne, "On the hydrophobic nature of signal sequences," May 15, 1981 *Eur. J. Biochem.* 116(2):419-422.

Von Heijne, "Signal sequences. The limits of variation," Jul. 5, 1985 *J. Mol. Biol.* 184(1):99-105.

Von Heijne and Abrahmsen, "Species-specific variation in signal sequence peptide design. Implications for protein secretion in foreign hosts," Feb. 27, 1989 *FEBS Lett.* 244(2):439-446.

Walter and Blobel, "Translocation of proteins across the endoplasmic reticulum III. Signal recognition protein (SRP) causes signal sequence-dependent and site-specific arrest of chain elongation that is released by microsomal membranes," Nov. 1, 1981 *J. Cell. Biol.* 91(2 Pt 1):557-561.

Walter and Johnson, "Signal sequence recognition and protein targeting to the endoplasmic reticulum membrane," 1994 *Ann. Rev. Cell Biol.* 10:87-119.

Watanabe and Blobel, "SecA protein is required for translocation of a model precursor protein into inverted vesicles of *Escherichia coli* plasma membrane," Oct. 1, 1993 *PNAS* 90:9011-9015.

Waters et al., "Protein translocation across the yeast microsomal membrane is stimulated by a soluble factor," Dec. 1, 1986 *J. Cell Biol.* 103(6 Pt 2):2629-2636.

Wessely et al., "Distinct roles of the receptor tyrosine kinases c-ErbB and c-Kit in regulating the balance between erythroid cell proliferation and differentiation," May 1997 *Cell Growth Diff.* 8(5):481-493.

Wickner and Schekman, "Protein translocation across biological membranes," Dec. 2, 2005 *Science* 310(5753):1452-1456.

Wiedmann et al., "Post-translational transport of proteins into microsomal membranes of *Candida* nialtosa," Jun. 1988 *EMBO J.* 7(6):1763-1768.

Wigg et al., "Assessment of cell concentration and viability of isolated hepatocytes using flow cytometry," Jun. 1, 2003 *Anal. Biochem.* 317(1):19-25.

Wikstrand et al., "Cell surface localization and density of the tumor-associated variant of the epidermal growth factor receptor, EGFRvIII," Sep. 15, 1997 *Cancer Res.* 57(18):4130-4140.

Williams, "Prof looks for parasite's 'Achilles heel'," in *University of Georgia Columns.* Jan. 27, 1997 UGA People. Available online [retrieved on Jul. 20, 2006]. Retrieved from the Internet: <http://www.uga.edu/columns/012797/peoplel.html>; 2 pgs.

Wissner et al., "Dual irreversible kinase inhibitors: quinazoline-based inhibitors incorporating two independent reactive centers with each targeting different cysteine residues in the kinase domains of EGFR and VEGFR-2," Jun. 1, 2007 *Bioorg. Med. Chem.* 15(11):3635-3648. Available online on Mar. 23, 2007.

Wolbring et al., "Inhibition of GTP-utilizing enzymes by tyrphostins," Sep. 9, 1994 *J. Biol. Chem.* 269(36):22470-22472.

Wright et al., "Pyrimidinone-peptoid hybrid molecules with distinct effects on molecular chaperone function and cell proliferation," Mar. 15, 2008 *Bioorg. Med. Chem.* 16(6):3291-3301. Available online on Dec. 14, 2007.

Xu et al., "Inhibition of protein tyrosine phosphorylation in T cells by a novel immunosuppressive agent, leflunomide," May 26, 1995 *J. Biol. Chem.* 270(21):12398-12403.

Yang et al., "Butein, a specific protein tyrosine kinase inhibitor," Apr. 17, 1998 *Bioc. Biophys. Res. Comm.* 245(2):435-438.

Yazici et al., "Dual inhibition of the epidermal growth factor and vascular endothelial growth factor phosphorylation for antivascular therapy of human prostate cancer in the prostate of nude mice," Nov. 1, 2005 *Prostate* 65(3):203-215. Available online on Jun. 9, 2005.

Yen et al., "Enhanced cell differentiation when RB is hypophosphorylated and down-regulated by radicicol, a SRC-kinase inhibitor," Sep. 1994 *Exp. Cell Res.* 214(1):163-171.

Yermovsky-Kammerer and Hajduk, "In vitro import of a nuclearly encoded tRNA into the mitochondrion of *Trypanosoma brucei*," Sep. 1999 *Mol. Cell Biol.* 19(9):6253-6259.

Yoneda et al., "The antiproliferative effects of tyrosine kinase inhibitors tyrphostins on a human squamous cell carcinoma in vitro and in nude mice," Aug. 15, 1991 *Cancer Res.* 51(16):4430-4435.

Zhang et al., "Hsp70 molecular chaperone facilitates endoplasmic reticulum-associated protein degradation of cystic fibrosis transmembrane conductance regulator in yeast," May 2001 *Mol. Biol. Cell* 12(5):1303-1314.

Zheng and Gierasch, "Signal sequences: the same yet different," Sep. 20, 1996 *Cell* 86(6):849-852.

Zheng and Nicchitta, "Structural determinants for signal sequence function in the mammalian endoplasmic reticulum," Dec. 17, 1999 *J. Biol. Chem.* 274(51):36623-36630.

Zheng et al., "Endosomes, glycosomes, and glycosylphosphatidylinositol catabolism in *Leishmania major*," Oct. 1, 2004 *J. Biol. Chem.* 279(40):42106-42113. Available online on Jul. 14, 2004.

Zheng et al., "Intracellular glycosylphosphatidylinositols accumulate on endosomes: toxicity of alpha-toxin to *Leishmania major*," Mar. 2005 *Eukaryot. Cell* 4(3):556-566.

Zheng et al., "Phosphotyrosine proteomic study of interferon α signaling pathway using a combination of immunoprecipitation and immobilized metal affinity chromatography," Jun. 2005 *Mol. Cell Proteomics* 4(6):721-730. Available online on Jan. 19, 2005.

Zhou and Xu, "Structural determinants of SecB recognition by SecA in bacterial protein translocation," Nov. 2003 *Nat. Struct. Biol.* 10(11):942-947. Available online on Sep. 28, 2003.

Zhu et al., "EGFR tyrosine kinase inhibitor AG1478 inhibits cell proliferation and arrests cell cycle in nasopharyngeal carcinoma cells," Aug. 10, 2001 *Cancer Lett.* 169(1):27-32.

Nwaka and Hudson, "Innovative lead discovery strategies for tropical diseases," Nov. 2006 *Nat. Rev. Drug. Discov.* 5(11):941-955. Available online on Oct. 13, 2006.

Nyrén and Strid, "The effect of equestin on energy-linked reactions in *Rhodospirilliuni rubrum* chromatophores," Feb. 1, 1989 *Arch. Biochem. Biophys.* 268(2):659-666.

O'Farrell et al., "SU11248 is a novel FLT3 tyrosine kinase inhibitor with potent activity in vitro and in vivo," May 1, 2003 *Blood* 101(9):3597-3605. Available online on Jan. 16, 2003.

Ohmichi et al., "The tyrosine kinase inhibitor tyrphostin blocks the cellular actions of nerve growth factor," May 4, 1993 *Biochem.* 32(17):4650. Available online on May 1, 1993.

Okamoto et al., "Expression of constitutively activated EGFRvIII in non-small cell lung cancer," Jan. 2003 *Cancer Sci.* 94:(1)50-56.

Oliver et al., "Azide-resistant mutants of *Escherichia coli* alter the SecA protein, an azide-sensitive component of the protein export machinery," Nov. 1990 *PNAS* 87(21):8227-8231.

Oliver et al., "Inhibition of mast cell FcεR1-mediated signaling and effector function by the Syk-selective inhibitor, piceatannol," Nov. 25, 1994 *J. Biol. Chem.* 269(47):29697-29703.

Oliver et al., "The Sec61 complex is essential for the insertion of proteins into the membrane of the endoplasmic reticulum," Apr. 3, 1995 *FEBS Lett.* 362:126-130.

Onoda et al., "Isolation of a novel tyrosine kinase inhibitor, lavendustin A, from *Streptomyces griseolavendus*," Nov.-Dec. 1989 *J. Nat. Prod.* 52(6):1252-1257. Available online on Nov. 1, 1989.

Oserov et al., "Selective inhibition of the epidermal growth factor and HER2/neu receptors by tyrphostins," May 25, 1993 *J. Biol. Chem.* 268(15):11134-11142.

Ouellette, "Biochemical and molecular mechanisms of drug resistance in parasites," Nov. 2001 *Trop. Med. Int. Health* 6(11):874-882.

Pannier et al., "Posttranslational protein transport in yeast reconstituted with a purified complex of Sec proteins and Kar2p," May 19, 1995 *Cell* 81(4):561-570.

Park et al., "AEE788, a dual tyrosine kinase receptor inhibitor, induces endothelial cell apoptosis in human cutaneous squamous cell carcinoma xenografts in nude mice," Mar. 1, 2005 *Clin. Cancer Res.* 11(5):1963-1973.

Parsons et al., "Distinct patterns of tyrosine phosphorylation during the life cycle of *Trypanosoma brucei*," Apr. 1990 *Mol. Biochem. Parasitol.* 45(2):241-248.

Parsons et al., "Protein kinases in divergent eukaryotes: identification of protein kinase activities regulated during trypanosome development," Apr. 1, 1993 *PNAS* 90(7):2656-2660.

Parsons et al., "*Trypanosoma congolense*: developmental regulation of protein kinases and tyrosine phosphorylation during the life cycle," May 1995 *Exp. Parasitol.* 80(3):507-514.

Patham et al., "Post-translational import of protein into the endoplasmic reticulum of a trypanosome: an in vitro system for discovery of anti-trypanosomal chemical entities," Apr. 15, 2009 *Biochem. J.* 419(2):507-517. Available online on Feb. 5, 2009.

Pays and Nolan, "Expression and function of surface proteins in *Trypaosoma brucei*," Mar. 1, 1998 *Mol. Biochem. Parasitol.* 91:3-36.

Pink et al., "Opportunities and challenges in antiparasitic drug discovery," Sep. 2005 *Nat. Rev. Drug Discov.* 4(9):727-740.

Plath et al., "Signal sequence recognition in posttranslational protein transport across the yeast ER membrane," Sep. 18, 1998 *Cell* 94(6):795-807.

Priest and Hajduk, "*Trypanosoma brucei* cytochrome $c_1$ is imported into mitochondria along an unusual pathway," Apr. 25, 2003 *J. Biol. Chem.* 278(17):15084-15094. Available online on Feb. 10, 2003.

"Protein Tyrosine Kinase Inhibitors," product datasheet. Calbiochem® Calbiochem-Novabiochem Corporation: San Diego, CA; copyright unknown. Available online [retrieved May 13, 2009]. Retrieved from the Internet: <http://www.emdbiosciences.com/SharedImages/TechnicalLiterature/1_CH0611_ptk.pdf>; 4 pgs.

Ramirez et al., "Heterologous expression of a *Trypanosoma cruzi* surface glycoprotein (gp82) in mammalian cells indicates the existence of different signal sequence requirements and processing," Nov.-Dec. 1999 *J. Eukaryot. Microbiol.* 46(6):557-565.

Ranta et al., "Reduced viability of human vascular endothelial cells cultured on Matrigel™," Jul. 1998 *J. Cell. Physiol.* 176(1):92-98.

Rapoport et al., "Protein transport across the eukaryotic endoplasmic reticulum and bacterial inner membranes," 1996 *Ann. Rev. Biochem.* 65:271-303.

Rapoport, "Protein translocation across the eukaryotic endoplasmic reticulum and bacterial plasma membranes," Nov. 29, 2007 *Nature* 450(7170):663-669.

Robinson et al., "The protein tyrosine kinase family of the human genome," Nov. 20, 2000 *Oncogene* 19(49):5548-5557.

Roskoski, "STI-571: an anticancer protein-tyrosine kinase inhibitor," Oct. 3, 2003 *Biochem. Biophys. Res. Comm.* 309(4):709-717.

Rudolph et al., "Determination of copy number of c-Myc protein per cell by quantitative Western blotting," Apr. 10, 1999 *Anal. Biochem* 269(1):66-71.

Rugo et al., "Phase I trial of the oral antiangiogenesis agent AG-013736 in patients with advanced solid tumors: pharmacokinetic and clinical results," Aug. 20, 2005 *J. Clin. Oncol.* 23(24):5474-5483. Available online on Jul. 18, 2005.

Rutkowski et al., "Signal sequences initiate the pathway of maturation in the endoplasmic reticulum lumen," Aug. 8, 2003 *J. Biol. Chem.* 278(32):30365-30372. Available online one May 27, 2003.

Ryan et al., "Intragenic reversion mutations that improve the export of maltose-binding protein in *Escherichia coli* malE signal sequence mutants," Mar. 5, 1986 *J. Biol. Chem.* 261(7):3389-3395.

Ryan and Edwards, "Systematic introduction of proline in a eukaryotic signal sequence suggests asymmetry within the hydrophobic core," Nov. 17, 1995 *J. Biol. Chem.* 270(46):27876-27879.

Saperstein et al., "Design of a selective insulin receptor tyrosine kinase inhibitor and its effect on glucose uptake and metabolism in intact cells," Jun. 27, 1989 *Biochemistry* 28(13):5694-5701. Available online on Jun. 1, 1989.

Sato et al., "A synthetic peptide corresponding to residues 137 to 157 of $p60^{v-src}$ inhibits tyrosine-specific protein kinases," Sep. 28, 1990 *Biochem. Biophys. Res. Comm.* 171(3):1152-1159.

Schatz and Dobberstein, "Common principles of protein translocation across membranes," Mar. 15, 1996 *Science* 271(5255):1519-1526.

Schmidt and Kiser, "SecA: the ubiquitous component of preprotein translocase in prokaryotes," Oct. 1999 *Microbes Infect.* 1(12):993-1004.

Selzer et al., "Cysteine protease inhibitors as chemotherapy: lessons from a parasite target," Sep. 28, 1999 *PNAS* 96(20):11015-11022.

Shawver et al., "Smart drugs: tyrosine kinase inhibitors in cancer therapy," Mar. 2002 *Cancer Cell* 1(2):117-123.

Sheader et al., "Variant surface glycoprotein RNA interference triggers a precytokinesis cell cycle arrest in African trypanosomes," Jun. 14, 2005 *PNAS* 102(24):8716-8721. Available online on Jun. 3, 2005.

Shushan et al., "The AG1478 tyrosine kinase inhibitor is an effective suppressor of leiomyoma cell growth," Sep. 2004 *Hum. Reprod.* 19(9):1957-1967. Available online on Jun. 17, 2004.

Simon et al., "Increased bioavailability of intravenous versus oral CI-1033, a pan erbB tyrosine kinase inhibitor: results of a phase I pharmcokinetic study," Aug. 1, 2006 *Clin. Cancer Res.* 12(15):4645-4651.

Sinyangwe et al., "Trypanocidal drug resistance in eastern province of Zambia," Jan. 30, 2004 *Vet. Parasitol.* 119(2-3):125-135. Available online on Jan. 13, 2004.

Smaill et al., "Tyrosine kinase inhibitors. 18. 6-substituted 4-anilinoquinazolines and 4-anilinopyrido[3,4-*d*]pyrimidines as soluble, irreversible inhibitors of the epidermal growth factor receptor," Feb. 1, 2001 *J. Med. Chem.* 44(3):429-440. Available online on Dec. 30, 2000.

Stanton et al., "Cysteine-less glycosylphosphatidylinositol-specific phospholipase C is inhibited competitively by a thiol reagent: evidence for glyco-mimecry by *p*-chloromercuriphenylsulphonate," 2002 *Biochem. J.* 366(pt. 1):281-288. Available online on May 15, 2002.

Stanton et al., "AUG-proximal nucleotides regulate protein synthesis in *Leishmania tropica*," Aug. 2006 *Mol. Microbiol.* 61(3):691-703. Available online on Jun. 20, 2006.

Steeghs et al., "Small molecule tyrosine kinase inhibitors in the treatment of solid tumors: an update of recent developments," Feb. 2007 *Ann. Surg. Oncol.* 14(2):942-953. Available online on Nov. 14, 2006.

Steff et al., "Detection of a decrease in green fluorescent protein fluorescence for the monitoring of cell death: an assay amenable to high-throughput screening technologies," Dec. 1, 2001 *Cytometry* 45(4):237-243.

Steverding et al., "Transferrin-binding protein complex is the receptor for transferrin uptake in *Trypanosoma brucei*," Dec. 1995 *J. Cell Biol.* 131(5):1173-1182.

Steverding and Scory, "*Trypanosoma brucei*: unexpected azide sensitivity of bloodstream forms," Oct. 2004 *J. Parasitol.* 90(5):1188-1190.

Stewart et al., "Trypanocidal activity of melamine-based nitroheterocycles," May 2004 *Antimicrob. Agents Chemother.* 48(5):1733-1738.

Stone, "FLT3 target practice," Aug. 15, 2004 *Blood* 104(4):915-916.

Strawn et al., "Flk-1 as a target for tumor growth inhibition," Aug. 1, 1996 *Cancer Res.* 56(15):3540-3545.

Subramanya et al., "Regulated cleavage of intracellular glycosylphosphatidylinositol in a trypanosome. Peroxisome-to-endoplasmic reticulum translocation of a phospholipase C," May 2006 *FEBS J.* 273(10):2110-2126.

Subramanya et al., "Glycosylphosphatidylinositol-specific phospholipase C regulates transferrin endocytosis in the African trypanosome," Feb. 1, 2009 *Biochem. J.* 417(3):685-694. Available online on Sep. 11, 2008.

SU5614 product datasheet [online]. Calbiochem: San Diego, CA; last revised on Oct. 5, 2007. Available online [retrieved on MAy 18, 2009]. Retrieved from the Internet: <http://www.emdbiosciences.com/Products/pds.asp?catno=572632>; 1 pg.

Sutent® (sunitib malate) product website [online]. Pfizer Oncology: New York, NY; Copyright 2007 [retrieved on May 13, 2009]. Retrieved from the Internet: <http://www.sutent.com/>; 2 pgs.

Akiyama et al. "Genistein, a Specific Inhibitor of Tyrosine-specific Protein Kinases", 1987. *Journal of Biological Chemistry.* 262(12):5592-5595.

Product Data Sheet. CDC-Chagas Disease-Biology. Centers for Disease Control and Prevention. Retrieved on Nov. 9, 2011. Retrieved from the Internet: http://www.cdc.gov/parasites/chagas/biology.html . 1 page.

Product Data Sheet. Parasites and Health. Trypanosomiasis, African. Last Modified Jul. 20, 2009. Retrived on Nov. 9, 2011. Retrieved from the Internet: http://www.dpd.cdc.gov. 2 pages.

* cited by examiner

TYROSINE KINASE INHIBITORS AS ANTI-KINETOPLASTID AGENTS

CONTINUING APPLICATION DATA

This application is the §371 U.S. National Stage of International Application No. PCT/US2007/024319, filed 21 Nov. 2001, which claims the benefit of U.S. Provisional Application Ser. No. 60/860,717, filed Nov. 22, 2006, each of which are incorporated by reference herein in their entireties.

BACKGROUND

Human African trypanosomiasis (HAT) occurs in 36 countries in Sub-Saharan Africa, threatening an estimated 60 million people with debilitating disease. No vaccines are available for prevention of infection by *Trypanosoma brucei*, which causes trypanosomiasis. Drugs in use are toxic, and drug resistance can be an issue (for review, see Docampo and Moreno, 2003, *Parasitol Res;* 90 Supp 1:S10-3). As a result, new and safer drugs are needed for the treatment of trypanosomiasis (Cowman and Crabb, 2003, *Trends Parasitol;* 19(11):538-43; Pink et al., 2005, *Nat Rev Drug Discov;* 4(9): 727-40; and Gelb and Hol, 2003, *Science;* 297(5580):343-4). In addition, additional new drugs must be developed, in order to prepare for possible emergence of drug resistance in the parasites (de Koning, 2001, *Int J Parasitol;* 31(5-6):512-22; Ouellette, 2001, *Trop Med Int Health;* 6(11):874-82; and Sinyangwe et al., 2004, *Vet Parasitol;* 119(2-3):12-35).

SUMMARY OF THE INVENTION

The present invention includes methods of killing, inhibiting the growth and/or inhibiting the reproduction of a kinetoplastid or apicomplexan protozoan, the method including contacting the protozoan with a tyrosine kinase inhibitor.

The present invention also includes methods of treating or preventing a kinetoplastid or apicomplexan protozoan infection in a subject, the method including administering to the subject an effective amount of a tyrosine kinase inhibitor.

The present invention includes methods of killing, inhibiting the growth and/or inhibiting the reproduction of a kinetoplastid or apicomplexan protozoan in a subject, the method including administering to the subject an effective amount of a tyrosine kinase inhibitor.

Also included in the present invention are compositions for treating or preventing a kinetoplastid or apicomplexan protozoan infection in a subject, the composition including an effective amount of two or more a tyrosine kinase inhibitors.

The present invention also includes compositions for treating or preventing a kinetoplastid or apicomplexan protozoan infection in a subject, the composition including an effective amount of one or more tyrosine kinase inhibitors and an effective amount of one or more conventional anti-kinetoplastid agents and/or one or more anti-apicomplexan therapeutic agents, wherein a conventional anti-kinetoplastid agent or anti-apicomplexan therapeutic agent is not a tyrosine kinase inhibitor.

With the methods and compositions of the present invention, the kinetoplastid protozoan may be of the genus *Trypanosoma*.

With the methods and compositions of the present invention, the kinetoplastid protozoan may be selected from *T. cruzi, T. brucei, T.b. gambiense,* and *T.b. rhodesiense.*

With the methods and compositions of the present invention, the kinetoplastid protozoan may be of the genus *Leishmania*.

With the methods and compositions of the present invention, the apicomplexan protozoan may be selected from *Falciparum, Toxoplasma gondii, cryptosporidia, Babesia microti, Babesia divergens,* and *Perkinsus marinus.*

With the methods and compositions of the present invention, the tyrosine kinase inhibitor may be selected from AG1478, A47, canertinib, sunitinib, axitinib, erlotinib, dasatinib, imatinib, nilotinib, sorafenib, lapatinib, and gefitinib.

With the methods and compositions of the present invention, the tyrosine kinase inhibitor may specifically inhibit only epidermal growth factor receptors (EGFR) tyrosine kinase activity. In some embodiments, the tyrosine kinase inhibitor may be selected from the group consisting of AG1478, A47, gefitinib, lapatinib, canertinib, and erlotinib.

With the methods and compositions of the present invention, the tyrosine kinase inhibitor may be a 4-anilinoquinazoline. In some embodiments, the 4-anilinoquinazoline is substituted at least one of the 2', 3', 4' positions of the aniline ring, including, substituents selected from an alkyl, aryl, phenylalkylamino, amino, halide, hydroxide, carboxyl, acyl, alkoxide, aryloxide, or alkylsulphide. In some embodiments, the 4-anilinoquinazoline is substituted at least one of the 5, 6, 7, 8 positions of the quinazoline ring, including substituents selected from an alkyl, aryl, phenylalkylamino, amino, halide, hydroxide, carboxyl, acyl, alkoxide, aryloxide, or alkylsulphide. In some embodiments, the tyrosine kinase inhibitor is 1,4-anilinoquinazoline wherein the aniline hydrogen has been replaced by an alkyl, phenyl or acyl group.

With the methods and compositions of the present invention, the tyrosine kinase inhibitor may specifically inhibit only epidermal growth factor receptors (EGFR) tyrosine kinase activity and is a 4-anilinoquinazoline.

With the methods and compositions of the present invention, the tyrosine kinase inhibitor may be a tyrphostin.

With the methods and compositions of the present invention, the tyrosine kinase inhibitor may be a pyrrolopyridine.

With the methods and compositions of the present invention, the tyrosine kinase inhibitor may inhibit multiple protein tyrosine kinases (PTK).

With the methods and compositions of the present invention, the tyrosine kinase inhibitor may inhibit vascular endothelial growth factor receptor (VEGFR) kinase activity.

With the methods and compositions of the present invention, the tyrosine kinase inhibitor may inhibit platelet-derived growth factor receptor (PDGFR) kinase activity.

With the methods and compositions of the present invention, the tyrosine kinase inhibitor may inhibit c-Abl tyrosine kinase activity.

With the methods and compositions of the present invention, the tyrosine kinase inhibitor may inhibit c-Src tyrosine kinase activity.

With the methods and compositions of the present invention, the tyrosine kinase inhibitor may inhibit c-Kit protein (c-Kit) kinase activity.

With the methods and compositions of the present invention, the tyrosine kinase inhibitor may inhibit FMS-like tyrosine kinase 3 (FLT3) tyrosine kinase activity.

With the methods and compositions of the present invention, the tyrosine kinase inhibitor may inhibit multiple protein tyrosine kinases (PTK).

With the methods and compositions of the present invention, the tyrosine kinase inhibitor may be selected from a small molecule, an antibody, and a receptor ligand.

The terms "comprises" and variations thereof do not have a limiting meaning where these terms appear in the description and claims.

Unless otherwise specified, "a," "an," "the," and "at least one" are used interchangeably and mean one or more than one.

DETAILED DESCRIPTION OF PREFERRED EMBODIMENTS OF THE INVENTION

Figure 1:
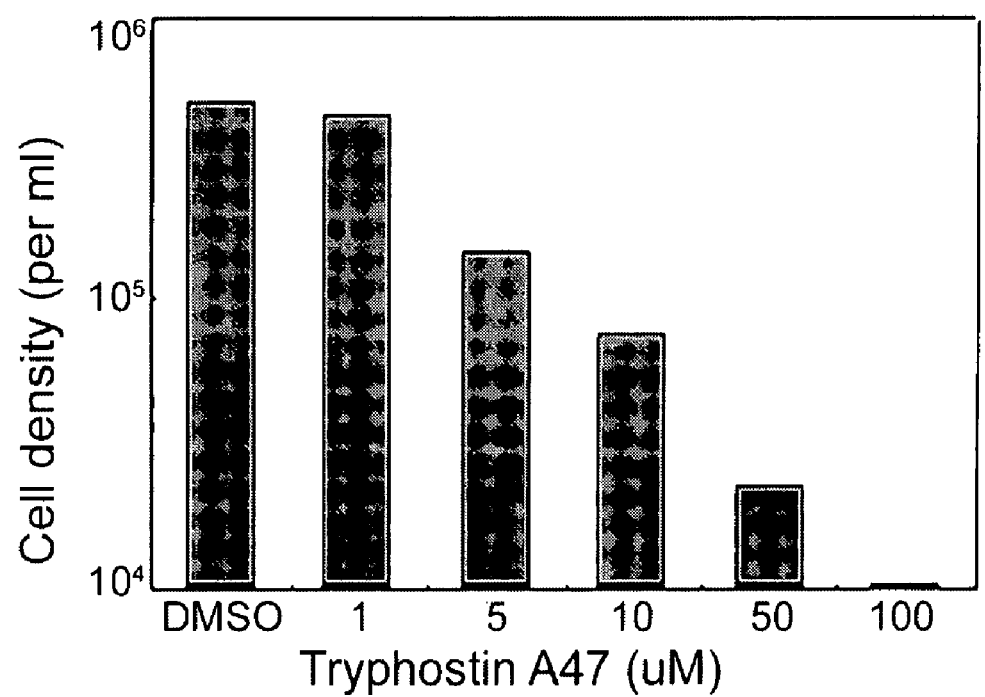
FIG. 1. The effect of Tyrphostin A47 on blood stream *T. brucei*.

With the present invention it has been found that the genome of the protozoan parasite *Trypanosoma brucei* includes sequences encoding proteins whose kinase domains are similar in sequence to the kinase domains of various protein tyrosine kinases, including the epidermal growth factor receptor (EGFR), the vascular endothelial cell growth factor receptor (VEGFR), c-Src protein (c-Src), c-Abl protein tyrosine kinase (c-Abl), c-Kit protein (c-Kit), and FMS-like tyrosine kinase 3 (FLT3). The present invention provides for the use of tyrosine kinase inhibitors as anti-protozoan agents, provides methods of killing, inhibiting the growth, and/or inhibiting the reproduction of a protozoan by contacting the protozoan with one or more tyrosine kinase inhibitors. Such contact may be in vitro, ex vivo, and/or in vivo, provides methods of treating or preventing a protozoan infection in a subject by administering to the subject an effective amount of one or more tyrosine kinase inhibitors. The present invention provides methods of killing, inhibiting the growth, and/or inhibiting the reproduction of a protozoan in a subject by administering to the subject an effective amount of one or more tyrosine kinase inhibitors. The present invention also provides compositions including tyrosine kinase inhibitors.

The methods and compositions of the present invention are applicable for a variety of protozoa, including, but not limited to, kinetoplastid and apicomplexan protozoa. Kinetoplastids are a group of flagellate protozoa, including a number of parasites responsible for serious diseases in humans and other animals, including economically relevant livestock, as well as various forms found in soil and aquatic environments. They are included in the *Euglenozoa*, and are distinguished from other such forms mainly by the presence of a kinetoplast, a DNA-containing granule located within the single mitochondrion and associated with the flagellar bases. Kinetoplastids typically have complex life-cycles involving more than one host, and go through various morphological stages. The most distinctive of these is the trypomastigote stage, where the flagellum runs along the length of the cell and is connected to it by an undulating membrane. Kinetoplastid protozoa, include, for example, protozoa of the *Blastocrithidia, Crithidia, Endotrypanum, Herpetomonas, Leishmania, Leptomonas, Phytomonas, Trypanosoma*, and *Wallaceina* genera. Diseases caused by trypanosomes include African Sleeping Sickness and South American Chagas Disease, from species of *Trypanosoma*, and *leishmaniasis*, from species of *Leishmania*.

Species of *Trypanosoma* to be treated by the present invention include, but are not limited to, *T. avium*, which causes trypanosomiasis in birds, *T. boissoni, T. brucei*, which causes sleeping sickness in humans and nagana in cattle, *T. carassii*, in freshwater teleosts, *T. cruzi*, which causes Chagas disease in humans, *T. gambiense, T. rhodesiense, T. congolense*, which causes nagana in cattle, horses, and camels, *T. equinum, T. equiperdum*, which causes dourine or covering sickness in horses, *T. evansi*, which causes one form of the disease surra in certain animals, *T. lewisi*, in rats, *T. melophagium, T. percae* in fish, *T. rangeli, T. rotatorium* in amphibian, *T. simiae, T. suis, T. theileri, T. triglae*, and *T. vivax*. In some embodiments of the present invention, species of *Trypanosoma* that infect humans or livestock are treated. In preferred embodiments, the protozoan is of the genus *Trypanosoma*, including, but not limited to, *T. cruzi, T. brucei, Tb. gambiense*, and *T.b. rhodesiense*. In one preferred embodiment of the present invention, the protozoan *T. brucei* is treated by the present invention.

Species of *Leishmania* to be treated by the present invention include, but are not limited to, *L. aethiopica, L. amazonensis, L. arabica, L. archibaldi, L. aristedesi, L. braziliensis, L. chagasi, L. colombiensis, L. deanei, L. donovani, L. enriettii, L. equatorensis, L. forattinii, L. garnhami, L. gerbili, L. guyanensis, L. herreri, L. hertigi, L. infantum, L. killicki L. lainsoni, L. major, L. mexicana, L. naiffi, L. panamensis, L. peruviana, L. pifanoi, L. shawi, L. tarentolae, L. tropica, L. turanica*, and *L. venezuelensis*.

The apicomplexa are an extremely large and diverse group of protozoa, characterized by the presence of a unique organelle called an apical complex. They are single-celled, spore-forming, and exclusively parasites of animals. Seven species infect humans (*Plasmodium, Babesia, Cryptosporidium, Isospora, Cyclospora, Sarcocystis*, and *Toxoplasma*). *Plasmodium*, as the causative agent of malaria, has a great impact on human health. Several apicomplexan parasites are also important in terms of veterinary medicine and agriculture. Most notable are *Babesia* and *Theileria* in cattle and *Eimeria* in poultry. Apicomplexan protozoans include, for example, *Babesia microti* and *Babesi divergens* (causing babesiosis), *Plasmodium* (causing malaria), (*Cryptosporidium parvum* (causing cryptosporidiosis), *Cyclospora cayetanensis* (causing cyclosporiasis), and *Toxoplasma gondii* (causing toxoplasmosis). The present invention includes, but is not limited to, the administration of tyrosine kinase inhibitors for the treatment of any of these various apicomplexan protozoa.

Tyrosine kinases are a class of enzymes that catalyze the transfer of the terminal phosphate of adenosine triphosphate (ATP) to tyrosine residues in peptide and protein substrates. Tyrosine kinases, by way of substrate phosphorylation, play critical roles in signal transduction for a number of cell functions and are important in the regulation of cell signaling. Tyrosine kinases are important contributing factors in, for example, cell proliferation, cell differentiation, and carcinogenesis. Thus, tyrosine kinases are an important class of enzymes as targets for therapeutic interventions.

As used herein, a tyrosine kinase inhibitor is an agent that interferes with the ability of a tyrosine kinase to function. Tyrosine kinase inhibitors of the present invention include agents that inhibit protozoan tyrosine kinase activity. Such agents may reduce, decrease, inhibit, and/or block the functioning of a protozoan tyrosine kinase. Tyrosine kinase inhibitors of the present invention include, but are not limited to, agents that inhibit the enzymatic activity of a kinase, agents bind to the ATP binding site of a tyrosine kinase, agents that bind to the substrate binding site of the tyrosine kinase, and agents that block or destabilize the dimerization of kinase enzyme subunits.

Tyrosine kinase inhibitors of the present invention inhibit the kinase activity of one or more protozoan tyrosine kinases.

A tyrosine kinase inhibitor of the present invention may exhibit less toxicity than currently used chemotherapeutic agents when administered to a subject. Such inhibitors may be identified or characterized by their effect on the catalytic activity of other, more well-characterized tyrosine kinases, such as, for example, one or more of the receptor tyrosine kinases (RTK) EGF, HER2, HER3, HER4, IR, IGF-1R, IRR, PDGFRα, PDGFRβ, TrkA, TrkB, TrkC, HGF, CSFIR, C-Kit, C-fms, Flk-1R, Flk4, KDR/Flk-1, Flt-1, FGFR-1R, FGFR-1R, FGFR-3R and FGFR-4R and/or one or more of the cellular tyrosine kinases (CTK) Src, Frk, Btk, Csk, Abl, Zap70, Fes, Fps, Fak, Jak, Ack, Yes, Fyn, Lyn, Lck, Blk, Hck, Fgr and Yrk. A tyrosine kinase inhibitor of the present invention may demonstrate selective activity against a narrowed spectrum of protein tyrosine kinases. For example, a tyrosine kinase inhibitor of the present invention may inhibit only one of the following receptor tyrosine kinases: EGF, HER2, HER3, HER4, IR, IGF-1R, IRR, PDGFRα, PDGFRβ, TrkA, TrkB, TrkC, HGF, CSFIR, C-Kit, C-fm, Flk-1R, Flk4, KDR/Flk-1, Flt-1, FGFR-1R, FGFR-1R, FGFR-3R, or FGFR-4R; or only one of the following cellular tyrosine kinases: Src, Frk, Btk, Csk, Abl, Zap70, Fes, Fps, Fak, Jak, Ack, Yes, Fyn, Lyn, Lek, Blk, Hck, Fgr or Yrk. In other aspects, a tyrosine kinase inhibitor of the present invention may inhibit only a subset of the above listed protein tyrosine kinases.

A tyrosine kinase inhibitor that inhibits the kinase activity of one or more protozoan tyrosine kinases can be identified and characterized by any of a variety of methods, including, but not limited to, any of a variety of known methods and any of those described herein. For example, the effect of a tyrosine kinase inhibitor on the catalytic activity of a protozoan tyrosine kinase may be evaluated in vitro, by incubating an in vitro culture of the protozoan with a tyrosine kinase inhibitor. Different concentrations of the inhibitor solubilized are added and living protozoan cells counted after exposure to the inhibitor. The mean and standard deviation of the cell count are plotted against inhibitor concentration. From the graphical plots, the concentration of the inhibitor that reduces protozoan cell density by 50% ($IC_{50}$) is determined. Any of the various in vitro cultures systems for kinetoplastid and apicomplexan protozoa may be used. The effect of a tyrosine kinase inhibitor on the catalytic activity of a protozoan tyrosine kinase may also be evaluated using any of a variety of various in vivo animals models that are available as models for kinetoplastid and apicomplexan protozoan disease, including livestock and human disease.

Further, the effect of a tyrosine kinase inhibitor on the catalytic activity of a protozoan tyrosine kinase may be evaluated by a determination of whether an inhibitor blocks the phosphorylation of tyrosine residues on protozoan proteins. Phosphorylated tyrosine resides (pTyr) can be detected on polypeptides with specific antibodies (Johnson and Hunter, 2005, *Nat Methods;* 2(1):17-25; Ignatoski, 2001, *Methods Mol Biol;* 124:39-48). For example, such a determination may be employed as follows. To cultured *T. brucei* 427 blood stream cells ($10^8$/ml, 5 ml) in 10-ml culture flasks, the inhibitor (10 μM final concentration) is added, and the cells incubated at 37° C. for 20 minutes. As a control, parasites are incubated in solvent alone and handled similarly. Proteins from *T. brucei* (50 μg per lane) (Parsons et al. 1993, *Proc Natl Acad Sci USA;* 90(7):2656-60) are separated by sodium dodecyl sulfate polyacrylamide gel electrophoresis (SDS-PAGE), and pTyr residues on the polypeptides detected with a mixture of anti-pTyr antibodies (for example, 4G10, PY20, and FB2) (Zheng et al., 2005, *Mol Cell Proteomics;* 4(6):721-30; Kumar et al., 2005, *Methods;* 35(1):9-21; Johnson and Hunter, 2005, *Nat Methods;* 2(1):17-25; Ignatoski, 2001, *Methods Mol Biol;* 124:39-48; Bleasdale et al., 2001, *Biochemistry;* 40(19):5642-54; Parsons et al., 1995, *Exp Parasitol;* 80(3):507-14; Parsons et al. 1993, *Proc Natl Acad Sci USA;* 90(7):2656-60; Wheeler-Alm and Shapiro, 1993, *Trop Med Parasitol;* 44(4):281-4; Parsons et al., 1991, *Mol Biochem Parasitol;* 45:241-248). The specificity of the antibody for pTyr is ascertained in a negative control experiment by inclusion of Tyr (40 mM final concentration) in the buffer for antibody binding to the trypanosome proteins (Parsons et al. 1993, *Proc Natl Acad Sci USA;* 90(7):2656-60). Quantitative pTyr western blots (Chopard et al., 2000, *Electrophoresis;* 21(3):517-22; Fradelizi et al., 1999, *Biotechniques;* 26(3): 484-6, 488, 490 passim; Rudolph et al., 1999, *Anal Biochem;* 269(1):66-71) are performed after lysing cells in buffer containing sodium orthovanadate (1 mM) which inhibits Tyr phosphatases (Johnson and Hunter, 2005, *Nat Methods;* 2(1): 17-25; Mustafa et al., 1997, *J Infect Dis;* 175(3):669-73), to determine possible reduction in the intensity of pTyr protein bands with or without inhibitor treatment of *T. brucei.*

Tyrosine kinase inhibitors include both protein and non-protein moieties. A tyrosine kinase inhibitor may be, for example, an antibody, a receptor ligand, or a small molecule inhibitor. A tyrosine kinase inhibitor may be in the form of a pharmaceutically acceptable salt, hydrate, solvate, crystal form, N-oxide(s), and/or individual diastereomer. In preferred embodiments, a tyrosine kinase inhibitor is a low molecular weight molecule, also referred to herein as a small molecule. The agent may, for example, be chemically synthesized, derived from a library of low molecular weight compounds, or derived from a library of extracts from plants or other organisms. Small molecule tyrosine kinase inhibitors may compete with the ATP-binding site of the catalytic domain of the target tyrosine kinase. Such inhibitors are generally orally active and have a favorable safety profile. A variety of small molecule tyrosine kinase inhibitors have been identified that possess antitumor activity and have been approved or are in clinical trials. These include, but are not limited to, gefitinib (IRESSA), sunitinib (SUTENT, SU11248), erlotinib (TARCEVA, OSI-1774), lapatinib (GW-572016), canertinib (CI 1033), semaxinib (SU5416), vatalanib (PTK787/ZK222584), sorafenib (BAY 43-9006), imatinib mesylate (GLEEVEC, ST1571), and leflunomide (SU101).

Tyrosine kinase inhibitors of the present invention also include derivatives and analogs of tyrosine kinase inhibitors. Such derivatives and analogs thereof may be identified by methods well know to the skilled artisan, for example, using computer modeling or combinatorial chemistry.

Tyrosine kinase inhibitors of the present invention include tyrphostins. Tyrphostins are synthetic, low molecular weight protein tyrosine kinase inhibitors, also known as AG compounds, that inhibit tyrosine kinase activity by binding to the substrate binding site. The tyrphostins include a systematic series of molecules with a progressive increase in affinity toward the substrate site of the EGF receptor kinase domain. See, for example, Gazit et al., 1989, *J Med Chem;* 32:2344-52, Twaddle et al., 1999, *J Surg Oncol;* 70(2):83-90, and Levitzki and Mishani, 2006, *Annu Rev Biochem;* 75:93-109. Tyrphostin tyrosine kinase inhibitors of the present invention include, but are not limited to, Tyrphostin A8 (Gazit et al., 1989, *J Med Chem;* 32:2344; Wohlberg et al., 1994, *J Biol Chem;* 269:22470), Tyrphostin A9 (Gazit et al., 1989, *J Med Chem;* 32:2344; Bider et al., 1991, *Am J Physiol;* 260:C721; Levitzki and Gilon, 1991, *Trends Pharmacol Sci;* 12:171), Tyrphostin A23 (Bider et al., 1991, *Am J Physiol;* 260:C721; Levitzki and Gilon, 1991, *Trends Pharmacol Sci;* 12:171), Tyrphostin A30 (Wessely et al., 1997, *Cell Growth Differen;*

8:481; Schwartz et al., 1995, *Oncol Res;* 7:277), Tyrphostin A25 (Gazit et al., 1989, *J Med Chem;* 32:2344; Wohlberg et al., 1994, *JBiol Chem;* 269:22470; Bider et al., 1991, *Am J Physiol;* 260:C721), Tyrphostin A46 (Gazit et al., 1989, *J Med Chem;* 32:2344; Gazit et al., 1991, *J Med Chem;* 34:1896), Tyrphostin A48 (Gazit et al., 1989, *J Med Chem;* 32:2344), Tyrphostin AG 126 (Gazit et al., 1989, *J Med Chem;* 32:2344; Bider et al., 1991, *Am J Physiol;* 260:C721; Novogrodsky et al., 1994 *Science;* 264:1319), Tyrphostin A51 (Levitzki, 1990, *Biochem Pharmacol;* 40:913), Tyrphostin A47 (Levitzki, 1990, *Biochem Pharmacol;* 40:913; Szende et al., 1995, *Cell Biol Int;* 19:903), Tyrphostin AG 370 (Bryckaert et al., 1992, *Nature Exp Cell Res;* 199:255), Tyrphostin B42 (Gazit et al., 1991, *J Med Chem;* 34:1896; Levitzki, 1990, *Biochem Pharmacol;* 40:913; Meydan et al., 1996, *Nature;* 379:645), Tyrphostin B48 (Gazit et al., 1991, *J Med Chem;* 34:1896), Tyrphostin B44(–) (Gazit et al., 1991, *J Med Chem;* 34:1896), Tyrphostin B46 (Gazit et al., 1991, *J Med Chem;* 34:1896), Tyrphostin B56 (Gazit et al., 1991, *J Med Chem;* 34:1896), Tyrphostin AG 825 (Levitzki and Gazit, 1995, *Science;* 267:1782; Osherov et al., 1993, *J Biol Chem;* 268:11134), Tyrphostin B50 (Gazit et al., 1991, *J Med Chem;* 34:1896), Tyrphostin AG 879 (Ohmichi et al., 1993, *Biochemistry;* 32:4650; Konrad et al., 1996, *J Biol Chem;* 271:24179), Tyrphostin AG 957 (Anafi et al., 1992, *J Biol Chem;* 267:4518) Tyrphostin AG1288 (Novogrodsky et al., 1994, *Science;* 264:1319), Tyrphostin AG1295 ((Levitzki and Gazit, 1995, *Science;* 267:1782; Kovalenko et al., 1994, *Cancer Res;* 54:6106), Tyrphostin AG1296 (Kovalenko et al., 1994, *Cancer Res;* 54:6106), Tyrphostin AG1433 (Kroll and Waltenberger, 1987, *J Biol Chem;* 272:32521; Strawn et al., 1996, *Cancer Res;* 56:3540), Tyrphostin AG1478 ((Levitzki and Gazit, 1995, *Science;* 267:1782; Zhu et al., 2001, *Cancer Lett;* 169(1):27-32; and Ellis et al., 2006, *Biochem Pharmacol;* 71(10):1422-34), RG-1302 (Yoneda et al., 1991, *Cancer Res;* 51:4430), RG-14620 (Yoneda et al., 1991, *Cancer Res;* 51:4430), Bis-Tyrphostin (Levitzki and Gilon, 1991, *Trends Pharmacol Sci;* 12:171), and derivatives and analogs thereof. A variety of tyrphostins, including, but not limited to, A47 and AG1478 are commercially available, for example, from Calbiochem.

A tyrosine kinase inhibitor of the present invention includes an inhibitor that inhibits the catalytic activity of one or more receptor tyrosine kinases (RTK) selected from EGF, HER2, HER3, HER4, IR, IGF-1R, IRR, PDGFRα, PDGFRβ, TrkA, TrkB, TrkC, HGF, CSFIR, C-Kit, C-fms, Flk-1R, Flk4, KDR/Flk-1, Flt-1, FGFR-1R, FGFR-1R, FGFR-3R and/or FGFR-4R.

In addition to the receptor tyrosine kinases, there also exists a family of entirely intracellular PTKs called "non-receptor tyrosine kinases" or "cellular tyrosine kinases" (CTK). CTKs do not contain extracellular and transmembrane domains. Over twenty-four CTKs in eleven subfamilies (Src, Frk, Btk, Csk, Abl, Zap70, Fes, Fps, Fak, Jak and Ack) have been identified. The Src subfamily of CTKs includes Src, Yes, Fyn, Lyn, Lck, Blk, Hck, Fgr and Yrk (Bolen, 1993, *Oncogene;* 8:2025-2031). A tyrosine kinase inhibitor of the present invention includes an inhibitor that reduces the catalytic activity of one or more cellular tyrosine kinases selected from Src, Frk, Btk, Csk, Abl, Zap70, Fes, Fps, Fak, Jak, Ack, Yes, Fyn, Lyn, Lck, Blk, Hck, Fgr and/or Yrk.

In some embodiments, a tyrosine kinase inhibitor of the present invention is an inhibitor that selectively inhibits the EGFR. In some embodiments, a tyrosine kinase inhibitor of the present invention inhibits only the EFGR. In some embodiments, a tyrosine kinase inhibitor of the present invention inhibits multiple tyrosine kinases. Examples of EGFR inhibitors include, for example, gefitinib, erlotinib, lapatinib, canertinib, sorafenib, and vandetanib. Examples of VEGFR inhibitors include, for example, axitinib, sunitinib, sematxinib, vatalanib, sorafenib, and vandetanib. Examples of PDGFR inhibitors include, for example, sunitinib, imatinib, sorafenib, and leflunomide. Examples of c-Kit inhibitors include, for example, sunitinib, imatinib, and semaxinib. Examples of FLT-3 inhibitors include, for example, sunitinib and semaxinib. Examples of BCR-ABL inhibitors include, for example, imatinib and dasatinib.

Tyrosine kinase inhibitors of the present invention include pyrimidine derivatives such as N-phenyl-2-pyrimidine-amine derivatives (U.S. Pat. No. 5,521,184 and WO 99/03854), indolinone derivatives and pyrrol-substituted indolinones (U.S. Pat. No. 5,792,783, EP 934 931, U.S. Pat. No. 5,834,504), U.S. Pat. Nos. 5,883,116, 5,883,113, 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. Nos. 3,772,295 and 4,343,940), 4-amino-substituted quinazolines (U.S. Pat. No. 3,470,182), 4-thienyl-2-(1H)-quinazolones, 6,7-dialkoxyquinazolines (U.S. Pat. No. 3,800,039), aryl and heteroaryl quinazoline (U.S. Pat. Nos. 5,721,237, 5,714,493, 5,710,158 and WO 95/15758), 4-anilinoquinazoline compounds (U.S. Pat. No. 4,464,375), and 4-thienyl-2-(1H)-quinazolones (U.S. Pat. No. 3,551,427).

4-anilinoquinazolines and 4-anilinoquinolines represent well known and important classes of protein kinase inhibitors, acting as ATP-competitive inhibitors of protein kinase enzymes. See, for example, Gosh et al., 1999, *Anticancer Drug Des;* 14(5):403-10; Denny, 2001, *Farmaco;* 56(1-2):51-6; Smaill et al., 2001, *J Med Chem;* 44(3):429-40; Assefa et al., 2003, *J Comput Aided Mol Des;* 17(8):475-93; Albuschat et al., 2004, *Eur J Med Chem;* 39(12):1001-11; Aparna et al., 2005, *J Chem Inf Model;* 45(3):725-38; Hennequin et al., 2006, *Bioorg Med Chem Lett;* 16(10):2672-6; Green et al., 2007, *J Med Chem;* 50(19):4728-45; and Liu et al., 2007, *Bioorg Med Chem Lett;* 17(22):6373-7. A tyrosine kinase inhibitor of the present invention may be a 4-anilinoquinazoline compound, a 4-anilinoquinoline compound, or a derivative thereof. Such compounds include, but are not limited to, 4-anilinoquinazoline compounds substituted at least one of the 2', 3', 4' positions of the aniline ring, including substituents selected from an alkyl, aryl, phenylalkylamino, amino, halide, hydroxide, carboxyl, acyl, alkoxide, aryloxide, or alkylsulphide. Such compounds include, but are not limited to, 4-anilinoquinazoline compounds substituted at least one of the 5, 6, 7, 8 positions of the quinazoline ring, including substituents selected form an alkyl, aryl, phenylalkylamino, amino, halide, hydroxide, carboxyl, acyl, alkoxide, aryloxide, or alkylsulphide. Such compounds include, but are not limited to, 4-anilinoquinazoline compounds wherein the aniline hydrogen has been replaced by an alkyl, phenyl or acyl group.

A tyrosine kinase inhibitor of the present invention includes gefitinib (N-(3-chloro-4-fluoro-phenyl)-7-methoxy-6-(3-morpholin-4-ylpropoxy) quinazolin-4-amine) (originally coded ZD1839). Gefitinib is a drug used in the treatment of certain types of cancer, acting in a similar manner to erlotinib (marketed as TARCEVA). It is marketed by AstraZeneca under the trade name IRESSA. Gefitinib is the first selective inhibitor of epidermal growth factor receptor's (EGFR) tyrosine kinase domain. The target protein (EGFR) is also sometimes referred to as Her1 or ErbB-1.

A tyrosine kinase inhibitor of the present invention includes dasatinib (N-(2-chloro-6-methylphenyl)-2-[[6-[4-(2-hydroxyethyl)-1-piperazinyl]-2-methyl-4-pyrimidinyl]

amino]-5-thiazole carboxamide monohydrate) (Das et al., 2006, *J Med Chem;* 49: 6819-32). Dasatinib, also known as BMS-354825, is a drug produced by Bristol-Myers Squibb and sold under the trade name SPRYCEL. Dasatinib is an oral dual BCR/ABL and Src family tyrosine kinases inhibitor approved for use in patients with chronic myelogenous leukemia (CML) and Philadelphia chromosome-positive acute lymphoblastic leukemia (Ph+ ALL). It is also being assessed for use in metastatic melanoma.

A tyrosine kinase inhibitor of the present invention includes erlotinib (N-(3-ethynylphenyl)-6,7-bis(2-methoxyethoxy)quinazolin-4-amine). Erlotinib (trade name TARCEVA, produced by Genentech/OSIP, originally coded as OSI-774) is a drug used to treat non-small cell lung cancer, pancreatic cancer and several other types of cancer. Similar to gefitinib, erlotinib specifically targets the epidermal growth factor receptor (EGFR) tyrosine kinase. It binds in a reversible fashion to the adenosine triphosphate (ATP) binding site of the receptor.

A tyrosine kinase inhibitor of the present invention includes imatinib (4-[(4-methylpiperazin-1-yl)methyl]-N-[4-methyl-3-[(4-pyridin-3-ylpyrimidin-2-yl)amino]-phenyl]-benzamide). Imatinib is currently used to treat certain types of cancer. It is currently marketed by Novartis as GLEEVEC in the USA and GLIVEC in Europe and Australia as its mesylate salt, imatinib mesilate. It is also referred to as CGP57148B or STI571. It is used in treating chronic myelogenous leukemia (CML), gastrointestinal stromal tumors (GISTs) and a number of other malignancies. Imatinib is a 2-phenylaminopyrimidine derivative that functions as a specific inhibitor of a number of tyrosine kinase enzymes. It occupies the TK active site, leading to a decrease in activity. Imatinib is specific for the TK domain in abl (the Abelson proto-oncogene), c-kit and PDGF-R (platelet-derived growth factor receptor).

A tyrosine kinase inhibitor of the present invention includes lapatinib (N-[3-chloro-4-[(3-fluorophenyl)methoxy]phenyl]-6-[5-[(2-methylsulfonylethylamino) methyl]-2-furyl]quinazolin-4-amine). Lapatinib, also known as lapatinib ditosylate or GW572016, is an anti-cancer drug developed by GlaxoSmithKline (GSK) as a treatment for solid tumors such as breast and lung cancer. It is marketed by GSK in the U.S. as TYKER and will be marketed as TYVERB in Europe. Lapatinib is an epidermal growth factor receptor (EGFR) and HER2/neu (ErbB-2) dual tyrosine kinase inhibitor. It binds to the intracellular phosphorylation domain to prevent receptor autophosphorylation upon ligand binding.

A tyrosine kinase inhibitor of the present invention includes nilotinib (4-methyl-N-[3-(4-methylimidazol-1-yl)-5-(trifluoromethyl) phenyl]-3-[(4-pyridin-3-ylpyrimidin-2-yDamino]benzamide). Nilotinib, in the form of the hydrochloride monohydrate salt, is a tyrosine kinase inhibitor approved as TASIGNA in the USA for drug-resistant chronic myelogenous leukemia (CML) also known by its clinical code AMN107 (Kantarjian et al., 2006, *N Engl J Med;* 354 (24):2542-51).

A tyrosine kinase inhibitor of the present invention includes sorafenib (4-[4-[[4-chloro-3-(trifluoromethyl)phenyl] carbamoylamino]phenoxy]-methyl-pyridine-2-carboxamide). Sorafenib, marketed as NEXAVAR by Bayer, is a drug approved for the treatment of advanced renal cell carcinoma (primary kidney cancer) and has received "Fast Track" designation by the FDA for the treatment of advanced hepatocellular carcinoma (primary liver cancer). It is a small molecular inhibitor of the Raf kinase, the PDGF kinase, the VEGF receptor 2 kinase, the VEGF receptor 3 kinase, and the c-Kit receptor for Stem cell factor.

A tyrosine kinase inhibitor of the present invention includes sunitinib (N-[2-(diethylamino)ethyl]-5-[(Z)-(5-fluoro-1,2-dihydro-2-oxo-3H-indol1-3-ylidine)methyl]-2,4-dimethyl-1H-pyrrole-3-carboxamide). Sunitinib, marketed as SUTENT, and also known as SU11248, is an oral, small-molecule, multi-targeted receptor tyrosine kinase (RTK) inhibitor approved by the FDA for the treatment of renal cell carcinoma (RCC) and imatinib-resistant gastrointestinal stromal tumor (GIST). See, for example, Cabebe and Wakelee, 2006, *Drugs Today;* 42(6):387-98). Sunitinib has become the standard of care for both of these cancers, and is currently being studied for the treatment of many others. Sunitinib inhibits cellular signaling by targeting multiple RTKs. These include all platelet-derived growth factor receptors (PDGF-R) and vascular endothelial growth factor receptors (VEGF-R), which play a role in both tumor angiogenesis and tumor cell proliferation. The simultaneous inhibition of these targets therefore leads to both reduced tumor vascularization and cancer cell death, and ultimately tumor shrinkage. Sunitinib also inhibits KIT. (CD 117) and other RTKs including RET, CSF-1R, and flt3.

A tyrosine kinase inhibitor of the present invention includes canertinib (N-[-4-[(3-chloro-4-fluorophenyl) amino]-7[3-(4-morpholinyl) propoxy]-6-quinazolinyl]-2-propenamide). Canertinib, also known as CI-1033 or PD183805, is the hydrochloride salt of an orally bio-available quinazoline with antineoplastic activities. Canertinib binds to the intracellular domains of epidermal growth factor receptor tyrosine kinases (ErbB family), irreversibly inhibiting their signal transduction functions and resulting in tumor cell apoptosis and suppression of tumor cell proliferation. Canertinib has been well tolerated in a variety of phase I schedules with some disease stabilization in patients with refractory metastatic breast cancer.

A tyrosine kinase inhibitor of the present invention includes axitinib (N-methyl-2-[[3-[1E-2-(pyridin-2-yl)ethenyl]-1H-inadazol-6-yl]sulfanyl]benzaminde). Axitinib, also known as AG-01376, is marketed by Pfizer and has demonstrated effectiveness for the treatment of thyroid cancer and pancreatic cancer, Axitinib works by selectively inhibiting vascular, endothelial growth factor (VEGFR) 1, 2, and 3.

A tyrosine kinase inhibitor of the present invention includes SU5416, also called semaxanib. SU5416, a small molecule drug developed by Sugen, is a potent and selective inhibitor of the vascular endothelial growth factor receptor (Flk-1/KDR) that inhibits tyrosine kinase catalysis, tumor vascularization, and growth of multiple tumor types. This agent can inhibit tumor growth in vivo in animal tumor models and is presently under evaluation in Phase I clinical studies for the treatment of human cancers (Fong et al., 1999, *Cancer Res;* 59(1):99-106).

Tyrosine kinase inhibitors of the present invention also include SU5614 (an inhibitor of VEGF (Flk-1) and PDGF receptor tyrosine kinases that does not have any effect on the EGF and IGF receptor tyrosine kinases), SU 11248 (an inhibitor FLT3) and ST1571 (an inhibitor c-Kit).

Tyrosine kinase inhibitors suitable for use in the methods of the present invention include any of those described herein. Examples of tyrosine kinase inhibitors suitable for use in the methods of the present invention include, but are not limited to, gefitinib, sunitinib, erlotinib, lapatinib, canertinib, semaxinib, vatalanib, sorafenib, imatinib, dasatinib, leflunomide, vandetanib, derivatives thereof, analogs thereof, and combinations thereof. Additional tyrosine kinase inhibitors suitable for use in the present invention are as described, for example, in U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340. Inhibitors of the present invention may be selected from the group consisting of 2-(3-amino)arylamino-4-aryl-thiazoles, pyrimidine derivatives, pyrrolopyrimidine derivatives, quinazoline derivatives, quinoxaline derivatives, pyrazoles derivatives, bis monocyclic, bicyclic or heterocyclic aryl compounds, vinylene-azaindole derivatives and pyridyl-quinolones derivatives, styryl compounds, styryl-substituted pyridyl compounds, seleoindoles, selenides, tricyclic polyhydroxylic compounds and benzylphosphonic acid compounds.

The present invention includes methods of killing, inhibiting the growth, and/or inhibiting the reproduction of a kinetoplastid or apicomplexan protozoan by contacting the protozoan with one or more tyrosine kinase inhibitors. Such contact may be in vitro, ex vivo, and/or in vivo. As used herein in vitro is in cell culture, ex vivo is a cell that has been removed from the body of a subject, and in vivo is within the body of a subject. As used herein, the term "subject" represents an organism, including, for example, an animal. An animal includes, but is not limited to, a human, a non-human primate, a horse, a pig, a goat, a cow, a rodent, such as, but not limited to, a rat or a mouse, or a domestic pet, such as, but not limited to, a dog or a cat.

The present invention includes methods of killing, inhibiting the growth, and/or inhibiting the reproduction of a kinetoplastid or apicomplexan protozoan in a subject by comprising administering to the subject an effective amount of one or more tyrosine kinase inhibitors. An agent may be administered in an amount effective to inhibit replication and/or growth of the protozoan. Agents of the present invention may be administered in an amount effective to kill a protzoan in an infected individual. Inhibition of the growth and reproduction of a protozoan and killing of an a protozoan may be determined by any of various known methods, including, but not limited to, the methods described in the examples herein. An agent of the present invention may be administered in an amount effective to inhibit tyrosine kinase activity of a protozoan kinase.

The present invention includes methods of treating or preventing a protozoan infection, such as a kinetoplastid or apicomplexan protozoan infection, in a subject by administering to the subject an effective amount of one or more agents that inhibit protozoan tyrosine kinase activity. Such an agent may be identified by the methods described herein. As used herein "treating" or "treatment" includes both therapeutic and prophylactic treatments. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. An agent may be administered to a subject to reduce the severity of the symptoms associated with a protozoan infection. Agents of the present invention may be taken as a prophylactic to prevent the development of a protozoan infection. An agent of the present invention may be administered to a subject to prevent the infection of a subject with a protozoan. An agent of the present invention may be administered to a subject prior to and/or after exposure to a protozoan.

The present invention includes compositions including one or more tyrosine kinase inhibitors. In some aspects, the present invention includes compositions including two or more tyrosine kinase inhibitors. Such compositions may be administered in any of the methods of the present invention. A composition may be a pharmaceutical composition. Such compositions may be formulated in a variety of forms adapted to the chosen route of administration. The formulations may be conveniently presented in unit dosage form and may be prepared by methods well known in the art of pharmacy. Formulations of the present invention include, for example, pharmaceutical compositions including a tyrosine kinase inhibitor and a pharmaceutically acceptable carrier. The phrase "pharmaceutically acceptable" refers to molecular entities and compositions suitable for use in contact with the tissues of humans and animals without undue toxicity, irritation, allergic response, and the like. The preparation of such compositions is well understood in the art. The formulations of this invention may include one or more accessory ingredients including, but not limited to, diluents, buffers, binders, disintegrants, surface active agents, thickeners, lubricants, preservatives, including, for example, antioxidants, and the like. Pharmaceutically acceptable includes salts, amides and esters that are well known in the art. Representative acid addition salts include, for example, hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts, and the like. Representative alkali or alkaline earth metal salts include, for example, aluminum, calcium, lithium, magnesium, potassium, sodium, or zinc salt, an ammonium salt such as a tertiary amine or quaternary ammonium salt, and an acid salt such as a succinate, tartarate, bitartarate, dihydrochloride, salicylate, hemisuccinate, citrate, isocitrate, malate, maleate, mesylate, hydrochloride, hydrobromide, phosphate, acetate, carbamate, sulfate, nitrate, formate, lactate, gluconate, glucuronate, pyruvate, oxalacetate, fumarate, propionate, aspartate, glutamate, or benzoate salt, and the like. Pharmaceutically acceptable carriers includes, for example, non-toxic, inert solid, semi-solid or liquid filler, diluent, encapsulating material or formulation auxiliary of any type. Examples of materials that may serve as pharmaceutically acceptable carriers include, but are not limited to, sugars, such as, for example, lactose, glucose and sucrose, starches such as, for example, corn starch and potato starch, cellulose and its derivatives such as, for example, sodium carboxymethyl cellulose, ethyl cellulose and cellulose acetate, powdered tragacanth, malt, gelatin, talc, excipients such as, for example, cocoa butter and suppository waxes, oils such as, for example, peanut oil, cottonseed oil, safflower oil, sesame oil, olive oil, corn oil and soybean oil, glycols, such as, for example, propylene glycol, polyols such as, for example, glycerin, sorbitol, mannitol and polyethylene glycol, esters such as, for example, ethyl oleate and ethyl laurate, agar, buffering agents such as, for example, magnesium hydroxide and aluminum hydroxide, alginic acid, pyrogen-free water, isotonic saline, Ringer's solution, ethyl alcohol and phosphate buffer solutions, as well as other non-toxic compatible substances used in pharmaceutical formulations. Wetting agents, emulsifiers and lubricants such as, for example, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Tyrosine kinase inhibitors of the present invention may be administered as compositions including one or more isolated inhibitors. As used herein, the term isolated means a preparation that is either removed from its natural environment or synthetically derived, for instance by recombinant techniques, or chemically or enzymatically synthesized. In a preferred form, the isolated tyrosine kinase inhibitors is purified and substantially free of other agents. The present invention also includes compositions including two or more tyrosine kinase inhibitors.

The inhibitors of the present invention can be administered by any suitable means including, but not limited to, for example, oral, rectal, nasal, topical (including, for example, transdermal, aerosol, buccal and sublingual), vaginal, or parenteral (including, for example, subcutaneous, intramuscular, intravenous, intradermal, intraperitoneal, intrasternal, and intraarticular injections as well as various infusion techniques). For parenteral administration in an aqueous solution, the solution may be suitably buffered if necessary and the liquid diluent first rendered isotonic with sufficient saline or glucose.

For enteral administration, the inhibitor may be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants.

Compositions for nasal administration may be formulated for aerosol or inhalation administration. Such compositions may include solutions in saline which may also contain, for example, benzyl alcohol or other suitable preservatives, absorption promoters to enhance bioavailability, and/or other solubilizing or dispersing agents such as those known in the art.

Compositions for rectal administration include, for example, suppositories which may contain a suitable non-irritating excipient, such as cocoa butter, synthetic glyceride esters or polyethylene glycols, which are solid at ordinary temperatures, but liquify and/or dissolve in the rectal cavity to release the drug.

Therapeutically effective concentrations and amounts may be determined for each application herein empirically by testing the compounds in known in vitro and in vivo systems, including, but not limited to, any of those described herein; dosages for humans or other animals may then be extrapolated therefrom. The efficacy of treatment may be assessed by any of various parameters well known in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA.

As used herein, a "subject" or an "individual" is an organism, including, for example, a mammal. A mammal may include, for example, a rat, mouse, a primate, a domestic pet (such as, but not limited to, a dog or a cat), livestock (such as, but not limited to, a cow, a horse, and a pig), or a human.

A tyrosine kinase inhibitor may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In accordance with the present invention, a tyrosine kinase inhibitor may be administered in combination with the administration of one or more previously known treatment modalities. As used herein, the term "additional therapeutic agent" represents one or more agents previously known to be effective for the treatment of a protozoan disease. Such an additional therapeutic agent is not a tyrosine kinase inhibitor. The administration of the tyrosine kinase may take place before, during, and/or after the administration of the other mode of therapy.

In some embodiments of the present invention, the administration of an inhibitor of tyrosine kinase in combination with additional therapeutic agents may demonstrate therapeutic synergy. Likewise, the administration of two or more tyrosine kinase inhibitors may demonstrate therapeutic synergy. As used herein, a combination may demonstrate therapeutic synergy if it is therapeutically superior to one or other of the constituents used at its optimum dose (Corbett et al., 1982, *Cancer Treatment Reports;* 66:1187. In some embodiments, a combination demonstrates therapeutic synergy if the efficacy of a combination is characterized as more than additive actions of each constituent.

By a "therapeutically effective amount" of a tyrosine kinase inhibitor is meant a sufficient amount of the compound to treat the subject at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including, for example, the disorder being treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts. Total daily dose of the compounds of this invention administered to a host in single or divided doses may be in amounts as determined by the attending physician, typically, for example, in amounts of from about 0.001 to 100 mg/kg body weight daily and preferably 0.01 to 10 mg/kg/day. As used herein, the terms "administration of a tyrosine kinase inhibitor" or "administering a tyrosine kinase inhibitor" refer to the act of providing a tyrosine kinase inhibitor or pharmaceutical composition thereof to the subject in need of treatment.

The present invention is illustrated by the following examples. It is to be understood that the particular examples, materials, amounts, and procedures are to be interpreted broadly in accordance with the scope and spirit of the invention as set forth herein. For any method disclosed herein that includes discrete steps, the steps may be conducted in any feasible order. And, as appropriate, any combination of two or more steps may be conducted simultaneously.

EXAMPLES

Example 1

Bioinformatic Analysis of the Protein Tyrosine Kinases in the *T. brucei* Genome New drugs are needed for treatment of human African trypanosomiasis (HAT), which is caused by the protozoan parasite *Trypanosoma brucei*. "Alternative Use Drug Discovery," whereby drugs that are approved for control of other ailments are tested as anti-parasite agents is a cost effective route for finding new anti-parasite drugs. In this example, the "Alternative Use" approach was applied to find new lead compounds that may be developed into drugs for treatment of HAT. To determine which class of drugs to focus on, a bioinformatic analysis was performed of the *T. brucei* genome sequence. This analysis revealed that the parasite contained proteins whose kinase domains are similar in sequence to that of the epidermal growth factor receptor (EGFR). This analysis also identified kinase domains in the *T. brucei* genome that are homologous to the kinase domains of the vascular endothelial cell growth factor receptor (VEGFR), c-Src protein (c-Src), c-Abl protein tyrosine kinase (c-Abl), c-Kit protein (c-Kit), and FMS-like tyrosine kinase 3 (FLT3).

Further, as presented in Example 2, it was determined that the 4-anilinoquinazoline, AG1478, which specifically inhibits EGFR kinase, killed *T. brucei*. A focused screen of other protein tyrosine kinase (PTK) specific anti-cancer drugs for trypanocidal activity was carried out in Examples 3 and 4, using cultured bloodstream *T. brucei*. As presented in Example 5, promising anti-trypanosome drugs will be evaluated for curing *T. brucei* infections in a murine model of HAT. This bioinformatics-informed drug discovery process will be extended to VEGFR, c-Src, and c-Abl because *T. brucei* encodes proteins with related kinase domains, and anti-cancer drugs that inhibit those enzymes are available. Many inhibitors of PTKs are being developed as drugs against cancer. The present invention will produce new lead compounds for anti-trypanosome drug discovery.

Example 2

Tyrosine Kinase Inhibitors Arrest Growth of Bloodstream *T. brucei*

New drugs are needed for treatment of infections by the trypanosomatid protozoans *Leishmania* and *Trypanosoma brucei*. However, the pathway for identifying new biological targets and developing new compounds that are specifically directed at the new targets can be tedious, drawn-out, expensive and frustrating (reviewed in Gelb and Hol, 2002, *Science;* 297:343-344 and Barrett and Barrett, 2000, *Parasitol Today;* 16:7-9). One possible shortcut to this traditional path for drug discovery involves "piggy-backing" on compounds that are already approved for treatments of other ailments or diseases and have gone through at least some phases of clinical trials.

Protein tyrosine kinases (PTKs) are important signaling molecules in eukaryotes (Robinson et al., 2000, *Oncogene;* 19:5548-5557; Wilks, 1993, *Adv Cancer Res;* 60:43-73; and Hubbard and Till, 2000, *Annu Rev Biochem;* 69:373-398). Recently, several inhibitors of PTKs, including the tyrphostins, have proven effective against certain cancers, and are currently in clinical trials as anti-cancer agents (Ellis et al., 2006, *Biochem Pharmacol;* 71:1422-1434; Zhu et al., 2001, *Cancer Lett;* 169:27-32; Twaddle et al., 1999, *J Surg Oncol;* 70:83-90; and Roskoski, 2003, *Biochem Biophys Res Commun;* 309:709-717). To explore the effectiveness of these anti-cancer drugs as anti-trypanosomal agents, two tyrphostins were tested using *Trypanosoma brucei* in an in vitro cell culture system. The PTK inhibitors, Tyrphostin A47 and Tyrphostin AG1478, were selected for initial evaluation. Tyrphostin A47 inhibits multiple PTKs, including EGFR (Turbov et al., 2002, *J Surg Oncol;* 79:17-29; Levitzki and Gazit, *Science,* 1995; 267:1782-8) and stops growth of HER14 transformed cells (Merkel et al., 1993, *Biochem Biophys Res Commun;* 192:1319-26; Lyall et al., 1989, *J Biol Chem;* 264:14503-9). Tyrphostin AG1478 is an anilinoquinazoline that inhibits EGFR kinase (Shushan et al., 2004, *Hum Reprod;* 19:1957-67; Zhu et al., 2001, *Cancer Lett;* 169:27-32). Several drugs whose structures similar to AG 1478 are used to treat human cancer. The results, summarized below indicate that inhibitors of trypanosomal PTKs can be developed as anti-trypanosome compounds.

Cultured trypanosomes (seeded at $10^4$/ml) in 100 µl of a 96-well plate received varying amounts of Tyrphostin A47 (Sigma). Parasites were counted with a haemocytometer after 48 hours in culture. Data are means of triplicate determinations, they are representative of three independent trials. Blood stream form of *T. brucei* were used for these studies since that stage of the parasite causes disease in humans. Inhibitory concentration 50 ($IC_{50}$) is the drug concentration which reduces the growth rate by 50%. Minimum inhibitory concentration (MIC) is the lowest concentration which killed all the parasites.

As shown in FIG. 1, Tyrphostin A47 kills *T. brucei*, with an $IC_{50}$ between 1 to 5 µM. Note that the y-axis in FIG. 1 uses a logarithmic scale.

*T. brucei* strain 427 was cultured axenically and seeded at $10^4$ cells/ml in 200 µl of medium a 96-well plate. Tyrphostin AG1478 (Sigma) (Zhu et al., 2001, *Cancer Lett;* 169:27-32; Shushan et al., 2004, *Hum Reprod;* 19:1957-1967) was added to the stated final concentrations, cells were incubated at 37° C. for 40 hours, and parasites were counted with a haemocytometer. Data are mean values representative of two independent trials each of which was performed in triplicate. *T. brucei* replicates every 8-10 hours.

Figure 2:
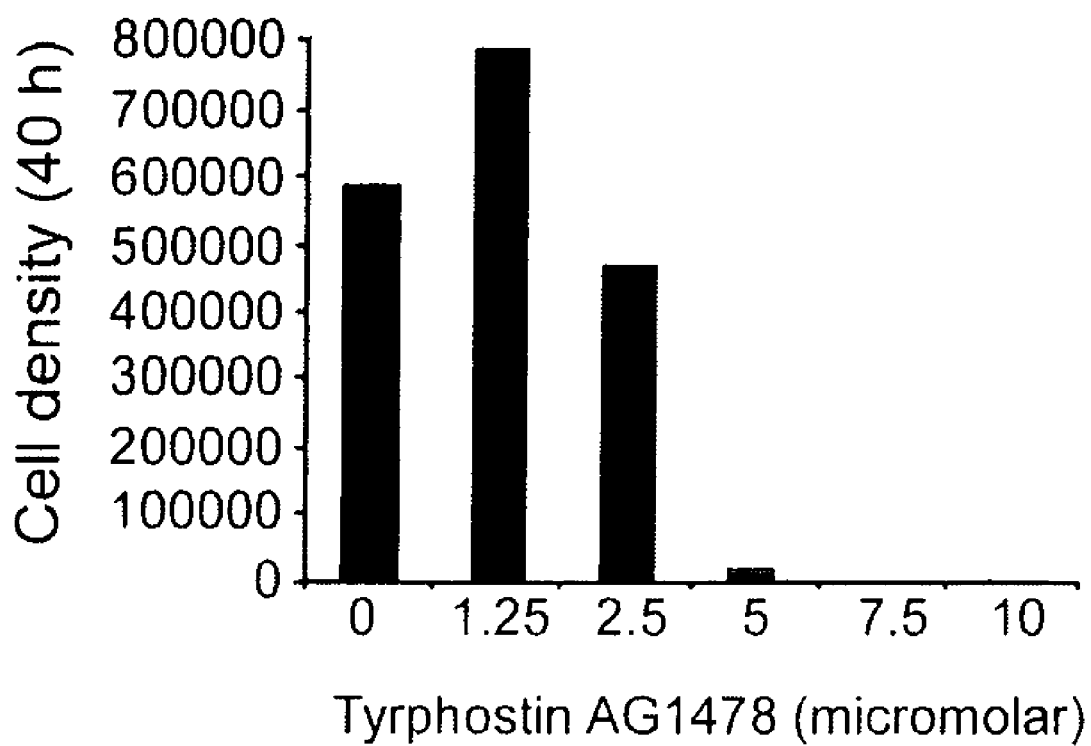
FIG. 2. Tyrphostin AG1478 inhibits *T. brucei* growth.

As shown in FIG. 2, Tyrphostin AG1478 inhibited growth of *T. brucei* bloodstream form. The $IC_{50}$ was between 2.5 to 5 µM.

The $IC_{50}$ of Tyrphostin A47 on *T. brucei* is in the range that arrests replication of transformed NIH3T3/HER14 cells (Merkel et al., 1993, *Biochem Biophys Res Commun;* 192: 1319-26; Lyall et al., 1989, *J Biol Chem;* 264:14503-9). AG1478, which is highly specific for EGFR kinase, also inhibited replication of *T. brucei* (FIG. 2). The $IC_{50}$ of AG1478 on *T. brucei* was between 2.5 to 5 µM, in the same range as the amount needed to arrest growth of human leiomyoma cells (Shushan et al., 2004, *Hum Reprod;* 19(9): 1957-67).

There are two implications from the data presented in FIG. 1 and FIG. 2. First, it appears that *T. brucei* contains an EGFR-like kinase activity, although the parasite lacks a "classic" EGFR. This observation is not entirely surprising because the ligand-binding region of EGFR is distinct from the kinase domain (reviewed in Linggi and Carpenter, 2006, *Trends Cell Biol;* 16:649-56). It is also interesting to note that many human cancer cells (e.g., glioblastomas and some breast cancer) express high levels of a mutant EGFR (named EGFRvIII) that lacks a ligand-binding domain. Remarkably, the PTK activity of EGFRvIII is constitutively activated in the absence of ligand (Okamoto, 2003, *Cancer Sci;* 94:50-6; Chu et al., 1997, *Biochem J;* 324(Pt 3):855-61; Wikstrand et al., 1997, *Cancer Res;* 57:4130-40; Batra et al., 1995, *Cell Growth Differ;* 6:1251-9). Thus, EGFRvIII is effectively a non-receptor Tyr kinase variant of EGFR. This example demonstrates that *T. brucei* has a Tyr kinase with an ATP binding site that is similar to that of EGFR kinase. Consistent with this theory, six TbPTKs have kinase domains with homology to that of the human EGFR, the target of AG1478. One or all of these TbPTKs could be inhibited by AG1478. Second, AG1478 is a 4-anilinoquinazoline. Since it kills *T. brucei*, the effect of other 4-anilinoquinazoline drugs, such as, for example, gefitinib, erlotinib, lapatinib, and canertinib, will be assayed for their trypanocidal effect (see Example 3).

These data from the two inhibitors tested in this example indicate that compounds directed against PTK's can be effective against trypanosome infection. Future experiments will test additional inhibitors of PTKs, including inhibitors known to be more potent against this class of enzymes, as anti-trypanosomal compounds.

Example 3

Effect of Canertinib and Erlotinib on *T. brucei* Viability

The 4-anilinoquinazoline canertinib (also referred to as CI-1033) is an inhibitor of EGFR kinase (Dewji, 2004, *J Chemotherapy;* 16(Suppl 4):44-48; Hamid, 2004, *J Am Pharm Assoc;* 44:52-58). To test the trypanocidal activity of canertinib, culture of blood stream *T. brucei* strain 427 was initiated in 24-well plates at $10^4$ cells/ml (in 500 μl of medium (Hirumi and Hirumi, 1991, *Parasitology;* 102(Pt 2):225-236)). Canertinib (Heymach et al., 2006, *Clin Cancer Res;* 12:4441s) (provided by Pfizer) was added to the stated final concentrations, and cells were incubated at 37° C. for 40 hours. Control cells received an equal volume of solvent (DMSO). Parasites were counted with a haemocytometer. Data plotted are mean values of quadruplicate determinations from one of three independent trials that produced similar results.

Figure 3:
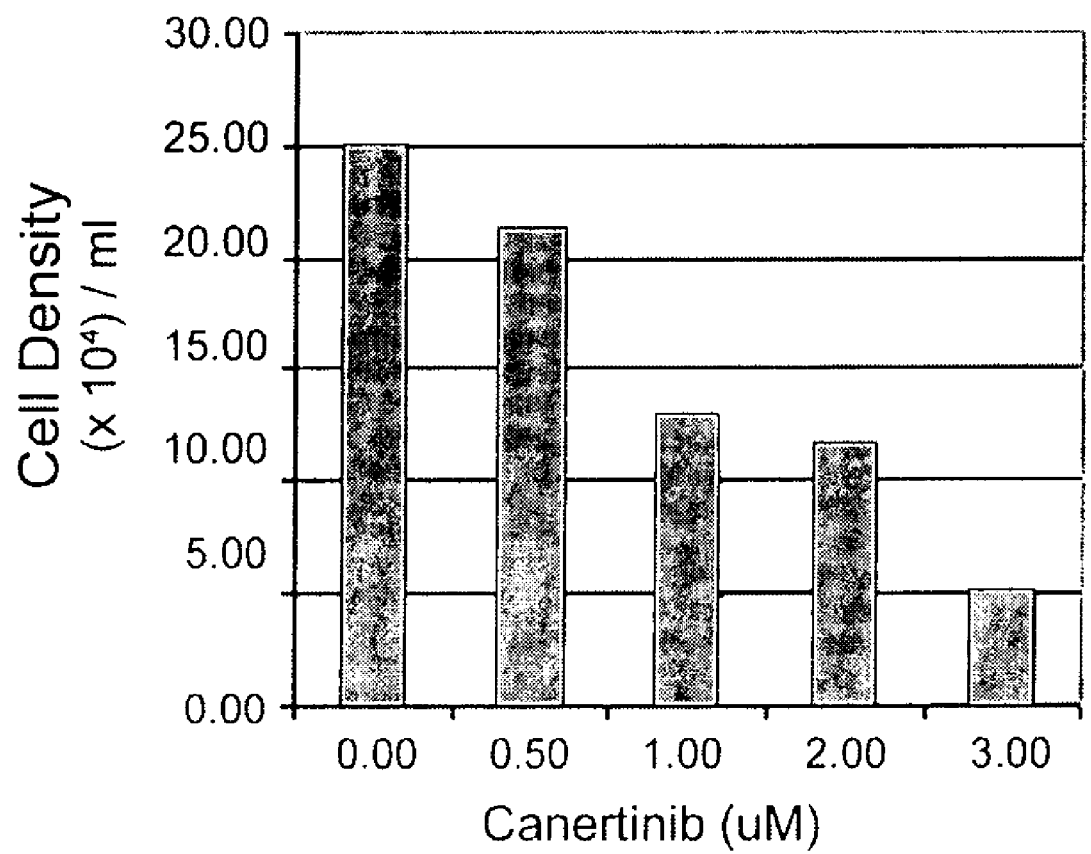
FIG. 3. Carnetinib kills *T. brucei*.

As show in FIG. 3, *T. brucei* are killed by canertinib ($IC_{50}$ of 1 μM). Above 4 μM of canertinib, all parasites were killed. Along with Example 2, these data further demonstrate that 4-anilinoquinazoline drugs can kill *T. brucei*. Inhibitors of protein tyrosine kinases are typically effective in the micromolar range when used on cells where ATP concentration is in the millimolar range (Knight and Shokat, 2005, *Chem Biol;* 12:621-637). Therefore, the concentration of canertinib needed to kill blood stream *T. brucei* is consistent with that expected for a susceptible cell. In vitro, when the drugs are used to inhibit purified enzymes, only micromolar amounts of ATP are used in the assays. Consequently the drugs, which compete for ATP binding sites of PTKs, are effective at nanomolar concentrations (Carter et al., 2005, *Proc Natl Acad Sci USA;* 102:11011-11016; reviewed in Knight and Shokat, 2005, *Chem Biol;* 12:621-637). Finally, it is noted that the plasma concentration of a 4-anilinoquinazoline can reach 10 μM (Ellis et al., 2006, *Biochem Pharmacol;* 71:1422-1434), a level that exceeds the amount required to kill all *T. brucei* in culture (FIG. 3). From these observations it is likely that canertinib will be effective against *T. brucei* infection of mice in an animal model of human African trypanosomiasis (HAT).

This example also determined that erlotinib (TARCEVA), a 4-anilinoquinazoline tyrosine kinase inhibitor is trypanocidal. erlotinib (TARCEVA), like canertinib, is an inhibitor of EGFR kinase (Bulgaru et al., 2003, *Expert Rev Anticancer Ther;* 3(3):269-79; Akita and Sliwkowski, 2003, *Semin Oncol;* 30(3 Suppl 7):15-24). The culture of blood stream *T. brucei* strain 427 was initiated in 24-well plates at $10^4$ cells/ml in 500 μl of medium (Hirumi and Hirumi, 1991, *Parasitology;* 102 Pt 2:225-236). Erlotinib (TARCEVA) (provided by Genentech/OSI), was added to the stated final concentrations shown in FIG. 4, and cells were incubated at 37° C. for 40 hours. Control cells received an equal volume of solvent (DMSO). Parasites were counted with a haemocytometer. Data plotted are mean values of quadruplicate determinations from one of three independent trials that produced similar results.

Figure 4:
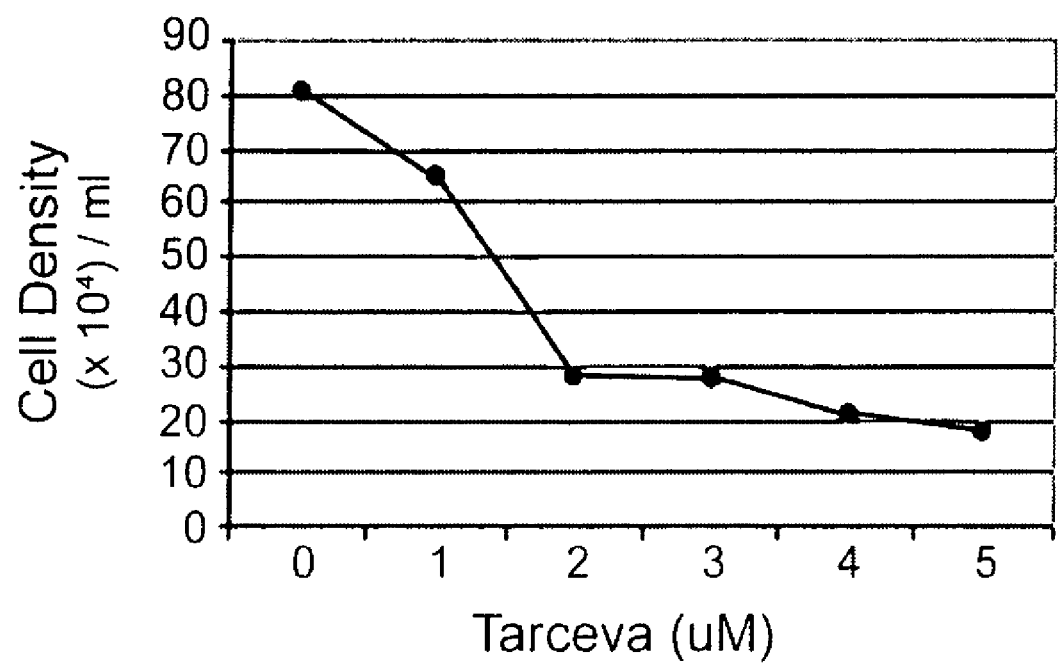
FIG. 4. Effect of TARCEVA (erlotinib) on *T. brucei* viability.

As shown in FIG. 4, erlotinib (TARCEVA) kills *T. brucei*. No parasites survived exposure to 10 μM of the drug. The $IC_{50}$ of TARCEVA against *T. brucei* is approximately 1.7 μM (FIG. 4). Thus, TARCEVA kills blood stream *T. brucei*. In human patients receiving a cycle of 150 mg/day TARCEVA, the plasma concentration of TARCEVA can reaches 60 μM (Broniscer et al., 2007, *Clin Cancer Res;* 13(5):1511-5), a level that exceeds the single does amount required to kill all *T. brucei* in this example (FIG. 4). A single dose of the drug yields a plasma concentration of 2 μM (Ling et al., 2006, *Drug Metab Dispos;* 34(3):420-6).

The trypanocidal effect of canertinib and erlotinib (TARCEVA), and any of the other inhibitors described herein, will be tested in animal models of human African trypanosomiasis (HAT), including mice infected with *T. brucei*, as described in Example 5 below.

Example 4

Sunitinib and Axitinib are Trypanocidal

Figure 5:
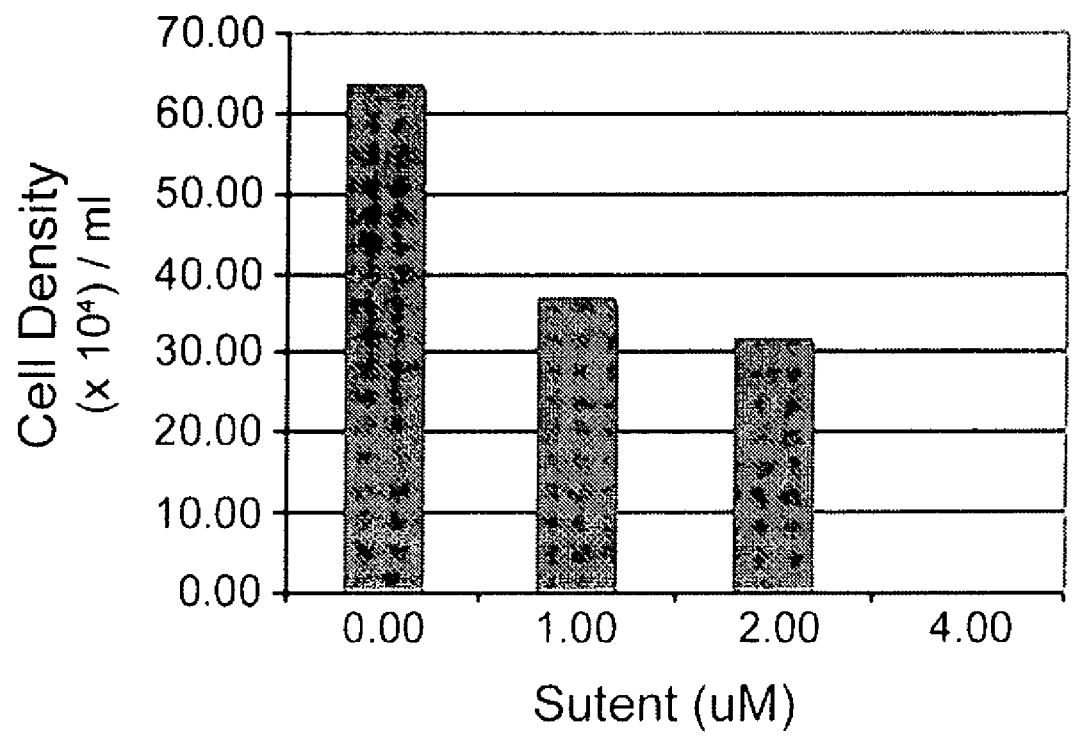
FIG. 5. SUTENT (sunitinib) kills *T. brucei*.
Figure 6:
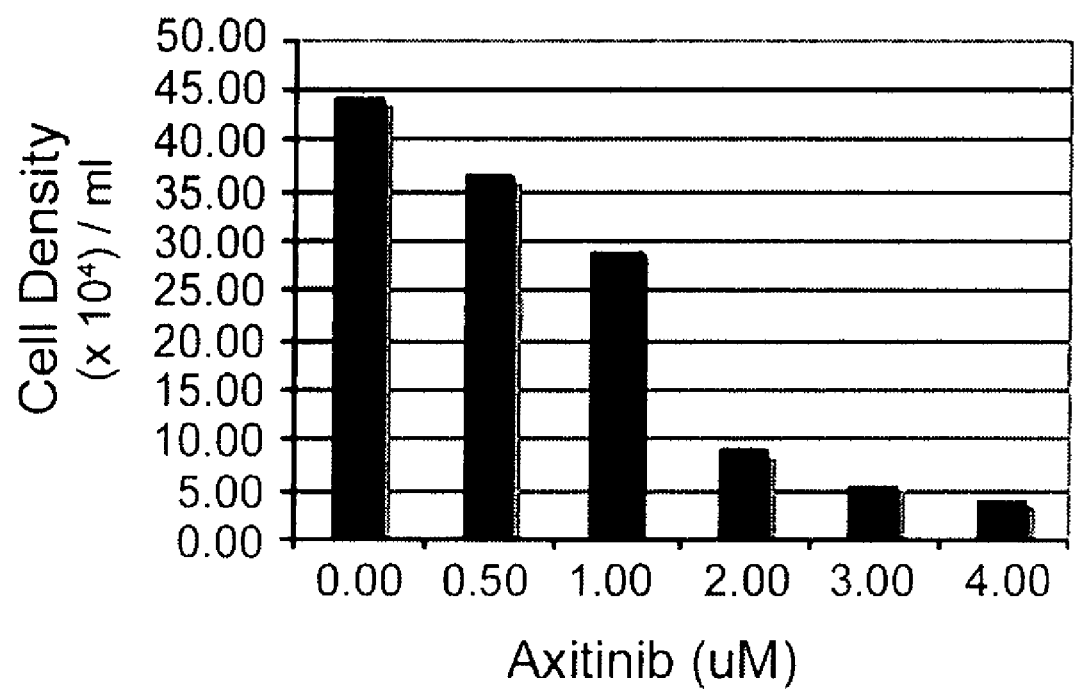
FIG. 6. Axitinib kills *T. brucei*.

This example presents data showing sunitinib and axitinib (both provided by Pfizer) are trypanocidal. Sunitinib (also known as SU11248 and marketed under the trade name SUTENT) inhibits VEGFR, PDGF, and c-Kit kinases (reviewed in Steeghs et al., 2007, *Ann Surg Oncol;* 14(2):942-53) and is approved by the Food and Drug Administration for treatment of renal cell carcinoma. The bioinformatics analysis of Example 1 indicated that the *T. brucei* genome encodes "VEGFR-like" kinase domains. Therefore, this example tests whether sunitinib (SUTENT) compromised *T. brucei* viability. To blood stream form *T. brucei* 427 (seeded at $10^4$ cells/ml in 500 μl of medium) sunitinib (SUTENT) (Abrams et al., 2003, *Mol Cancer Ther;* 2:471-478; Mendel et al., 2003, *Clin Cancer Res;* 9:327-337) was added to the stated final concentrations and cells were incubated at 37° C. for 40 hours. Parasites were counted with a haemocytometer. Data plotted are mean values of quadruplicate determinations from a representative experiment. FIG. 5 shows that SUTENT kills *T. brucei*. SUTENT kills *T. brucei* at low micromolar levels, indicating that VEGFR, PDGF, and c-Kit kinase domains may be targeted for anti-trypanosome drug discovery. Using the procedures described above, as shown in FIG. 6, axitinib (also known as AG-013736) also kills *T. brucei*.

Example 5

Use of *T. brucei rhodesiense* for Mouse Infection Studies

Following guidelines of the World Health Organization (WHO) parasite drug discovery initiative (see Nwaka and Hudson, 2006, *Nat Rev Drug Discov;* 5:941-955 and Nwaka and Ridley, 2003, *Nat Rev Drug Discov;* 2:919-928 for reviews) the candidate trypanocidal drugs of the present invention will be tested in animal models for both acute and late stage HAT. Work with *T. brucei* 427 will predict effectiveness of drugs against acute stage disease. For a model of late stage disease, *T. brucei rhodesiense* STIB 900 infection of mice will be studied. *T. b. rhodesiense* STIB 900 infection in mice is thought to mimic late stage disease (Dardonville et al., 2006, *J Med Chem;* 49:3748-3752) because it does not respond to drugs used in treating acute stage (e.g., pentamidine) (Docampo and Moreno, 2003, *Parasitol Res;* 90(Supp 1):S10-13); instead the infection is cured with melarsoprol, a toxic arsenical, which is used in treatment of late stage HAT. (Stewart et al., 2004, *Antimicrob Agents Chemother;* 48:1733-1738). Thus, a cure of *T. b. rhodesiense* STIB 900 infection may signal that the drugs that we are studying could cure late stage HAT. (Nwaka and Hudson, 2006, *Nat Rev Drug Discov;* 5:941-955; Nwaka and Ridley, 2003, *Nat Rev Drug Discov;* 2:919-928). Drugs will be administered to mice by gavage (i.e., forced feeding) because all of them are orally bioavailable (Rugo et al., 2005, *J Clin Oncol;* 23:5474-5483; Kim et al., 2006, *J Clin Endocrin Metab;* 91:4070-4076; Simon et al., 2006, *Clin Cancer Res;* 12:4645-4651; and Gridelli et al., 2007, *The Oncologist;* 12:191-200; reviewed in Steeghs et al., 2007, *Ann Surg Oncol;* 14(2):942-53).

PTK Inhibitor anti-trypanosome drugs are likely to be very valuable in the field. The urgent need for new anti-trypanosome drugs cannot be overstated (reviewed in Nwaka and Hudson, 2006, *Nat Rev Drug Discov;* 5:941-955; Nwaka and Ridley, 2003, *Nat Rev Drug Discov;* 2:919-928; and Gelb and Hol, 2002, *Science;* 297:343-344). Current anti-trypanosome drugs are toxic, and must be injected intramuscularly in a clinic (reviewed in Docampo and Moreno, 2003, *Parasitol Res;* 90(Supp 1):S10-13 and Fairlamb, 2003, *Trends Parasitol;* 19:488-494). Unfortunately, in those areas of rural Africa where HAT. is endemic, clinics are not commonplace. Fortunately, the drugs of the present invention are well-tolerated, with minimal side effects in human clinical trials, and can be administered by swallowing (Rugo et al., 2005, *J Clin Oncol;* 23:5474-5483; Kim et al., 2006, *J Clin Endocrin and Metab;* 91:4070-4076; Simon et al., 2006, *Clin Cancer Res;* 12:4645-4651; and Gridelli et al., 2007, *The Oncologist;* 12:191-200).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention claimed is:

1. A method of killing and/or inhibiting the growth of the bloodstream form of a kinetoplastid protozoan of the genus *Trypanosoma*, the method comprising contacting the protozoan with a tyrosine kinase inhibitor; wherein the tyrosine kinase inhibitor is a 4-anilinoquinazoline or tyrphostin selected from the group consisting of canertinib, sunitinib, axitinib, dasatinib, and nilotinib.

2. A method of treating a protozoan infection in a subject, the method comprising administering to the subject an effective amount of a tyrosine kinase inhibitor; wherein the tyrosine kinase inhibitor is a 4-anilinoquinazoline or tyrphostin selected from the group consisting of canertinib, sunitinib, axitinib, dasatinib, and nilotinib.

3. A method of killing and/or inhibiting the growth of the blood stream form of a kinetoplastid protozoan of the genus *Trypanosoma* in a subject, the method comprising administering to the subject an effective amount of a tyrosine kinase inhibitor; wherein the tyrosine kinase inhibitor is a 4-anilinoquinazoline or tyrphostin selected from the group consisting of canertinib, sunitinib, axitinib, dasatinib, and nilotinib.

4. The method of claim 1, wherein the kinetoplastid protozoan is selected from the group consisting of *T. cruzi, T. brucei, T.b. gambiense*, and *T.b. rhodesiense.*

5. The method of claim 1, wherein the tyrosine kinase inhibitor specifically inhibits epidermal growth factor receptors (EGFR) tyrosine kinase activity.

6. The method of claim 1, wherein the tyrosine kinase inhibitor inhibits vascular endothelial growth factor receptor (VEGFR) kinase activity.

7. The method of claim 2, wherein the protozoan is selected from the group consisting of *T. cruzi, T. brucei, T.b. gambiense*, and *T.b. rhodesiense.*

8. The method of claim 3, wherein the kinetoplastid protozoan is selected from the group consisting of *T. cruzi, T. brucei, T.b. gambiense*, and *T.b. rhodesiense.*

9. The method of claim 2, wherein the tyrosine kinase inhibitor specifically inhibits epidermal growth factor receptors (EGFR) tyrosine kinase activity.

10. The method of claim 3, wherein the tyrosine kinase inhibitor specifically inhibits epidermal growth factor receptors (EGFR) tyrosine kinase activity.

11. The method of claim 2, wherein the tyrosine kinase inhibitor inhibits vascular endothelial growth factor receptor (VEGFR) kinase activity.

* * * * *